(12) United States Patent
Rogozinski

(10) Patent No.: US 11,849,980 B2
(45) Date of Patent: Dec. 26, 2023

(54) SYSTEM AND METHOD FOR THE TREATMENT OF SPINAL CONDITIONS

(71) Applicant: Chaim Rogozinski, Jacksonville, FL (US)

(72) Inventor: Chaim Rogozinski, Jacksonville, FL (US)

(*) Notice: Subject to any disclaimer, the term of this patent is extended or adjusted under 35 U.S.C. 154(b) by 479 days.

(21) Appl. No.: 16/909,275

(22) Filed: Jun. 23, 2020

(65) Prior Publication Data

US 2021/0322062 A1 Oct. 21, 2021

Related U.S. Application Data

(60) Provisional application No. 62/987,938, filed on Mar. 11, 2020.

(51) Int. Cl.
*A61B 17/70* (2006.01)
*A61B 17/80* (2006.01)

(52) U.S. Cl.
CPC ...... *A61B 17/7044* (2013.01); *A61B 17/7011* (2013.01); *A61B 17/7049* (2013.01); *A61B 17/7059* (2013.01)

(58) Field of Classification Search
CPC ............. A61B 17/8023; A61B 17/701; A61B 17/7007; A61B 17/7049; A61B 17/705; A61B 17/7052; A61B 17/7044; A61B 17/7058
USPC ......................................................... 606/71
See application file for complete search history.

(56) References Cited

U.S. PATENT DOCUMENTS

| | | | |
|---|---|---|---|
| 4,455,011 A * | 6/1984 | Levine ..................... | H02K 5/26 248/646 |
| 5,102,412 A | 4/1992 | Rogozinski | |
| 5,181,917 A | 1/1993 | Rogozinski | |
| 5,607,425 A | 3/1997 | Rogozinski | |
| 5,716,357 A | 2/1998 | Rogozinski | |
| 5,904,682 A | 5/1999 | Rogozinski | |
| 6,010,504 A | 1/2000 | Rogozinski | |
| 6,017,343 A | 1/2000 | Rogozinski | |
| 6,019,759 A * | 2/2000 | Rogozinski ........ | A61B 17/7041 606/308 |
| 6,336,927 B2 | 1/2002 | Rogozinski | |
| 6,355,038 B1 | 3/2002 | Pisharodi | |
| 6,379,354 B1 | 4/2002 | Rogozinski | |

(Continued)

*Primary Examiner* — Jan Christopher L Merene
(74) *Attorney, Agent, or Firm* — Brian J. Colandreo; Heath M. Sargeant; Holland & Knight LLP

(57) ABSTRACT

A multi-link bone fixation assembly and method having interconnected longitudinal linking members, end caps and locknuts, and possibly transverse linking members, all disposed on implanted bone fasteners, the assembly providing a rigid, fixed ladder or frame to preclude relative movement between vertebrae or bone. At least two of the end caps and both ends of at least one of the transverse linking members are slotted such that, in the event a previously implanted assembly needs to be lengthened, additional bone fasteners are implanted, and the end caps and/or transverse linking members are removed from the assembly in a direction perpendicular to the axis of the bone fastener by loosening rather than removing the locknuts from the bone fasteners. The new longitudinal linking members are then inserted onto the bone fasteners in a direction perpendicular to the axis and the locknuts are tightened to secure the now-extended assembly.

11 Claims, 23 Drawing Sheets

(56) References Cited

U.S. PATENT DOCUMENTS

| | | | |
|---|---|---|---|
| 6,626,909 B2* | 9/2003 | Chin | A61B 17/7059 |
| | | | 606/279 |
| 6,669,697 B1* | 12/2003 | Pisharodi | A61B 17/701 |
| | | | 606/264 |
| 7,766,943 B1 | 8/2010 | Fallin et al. | |
| 2001/0034521 A1* | 10/2001 | Bailey | A61B 17/7007 |
| | | | 606/267 |
| 2006/0089645 A1* | 4/2006 | Eckman | A61B 17/7011 |
| | | | 606/279 |
| 2007/0270820 A1* | 11/2007 | Dickinson | A61B 17/7007 |
| | | | 606/279 |
| 2008/0287994 A1* | 11/2008 | Perez-Cruet | A61B 17/701 |
| | | | 606/301 |
| 2010/0036420 A1* | 2/2010 | Kalfas | A61B 17/7049 |
| | | | 606/264 |
| 2011/0245880 A1* | 10/2011 | Lawrence | A61B 17/8863 |
| | | | 606/279 |
| 2015/0100089 A1* | 4/2015 | Richelsoph | A61B 17/7011 |
| | | | 606/246 |
| 2019/0099205 A1* | 4/2019 | Pisharodi | A61B 17/7043 |

* cited by examiner

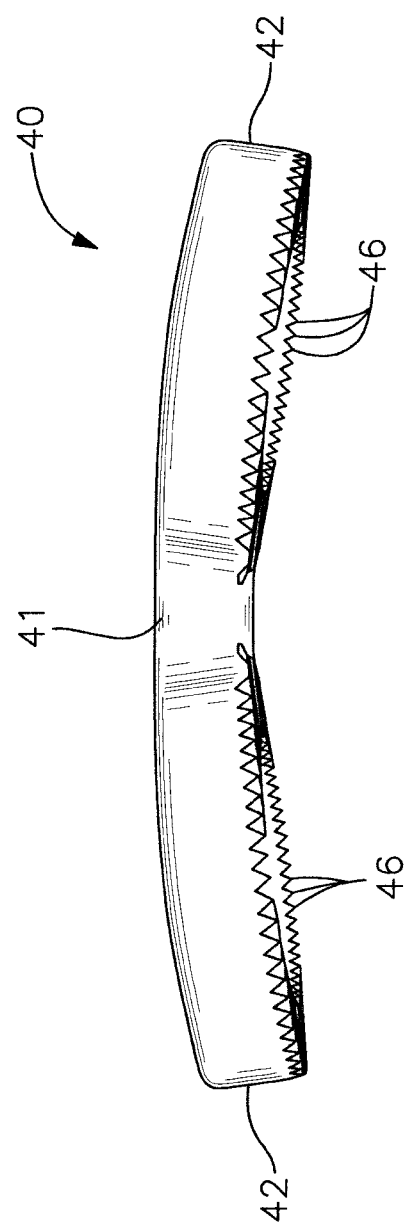

SYSTEM AND METHOD FOR THE TREATMENT OF SPINAL CONDITIONS

BACKGROUND OF THE INVENTION

This invention relates generally to apparatus and methods for treating and correcting spinal abnormalities or conditions, stabilizing the position of the spine and vertebrae thereof and fixing or moving the position of vertebrae. More specifically, the present invention provides an apparatus and system which includes a plurality of links usable together under various circumstances to treat, for example, different spinal curvature conditions or bone fractures.

The prior art includes many different apparatuses and methods for treating spinal conditions or bone fractures. Known apparatuses utilize elongate plate members having several aligned openings or an elongated slot therein for receiving screws or bolts that are affixed to vertebrae. The plate is secured to the screws or bolts and exerts force on the selected vertebra or vertebrae to move same into a desired position or to maintain same in a desired position.

In using such known plate systems, a problem arises when the points on the vertebrae defined by the screws or bolts are not collinear, i.e., they do not lie in a straight line. This creates a problem for the physician because the openings in the plate are collinear and, therefore, the screws do not line up with the plate openings. The physician has several options to compensate for such nonalignment, all of which present additional problems themselves. The plate can be contoured in the frontal plane to attempt to line the screws up with the plate openings. Due to the thickness and high strength of the plate, this is essentially impossible to do intraoperatively. Another option is to bend the screws or bolts so that they fit in the slots or openings in the plate. This creates an immediate high stress region in the screw or bolt which can cause failure of the same upon cyclical loading or, even worse, can lead to a fracture of the bone, pedicle or the vertebra.

A third option is to place the screws or bolts in a less than optimum position or trajectory in the pedicle or the vertebrae so that they line up with the plate openings. This too can lead to pedicle or vertebrae fractures or cut-out, as well as nerve root injury.

Other known apparatuses for treating spinal deformities are disclosed in U.S. Pat. Nos. 5,102,412 and 5,181,917. These apparatus include elongate rod members which have vertebra engaging means secured thereto in an adjustable fashion. The apparatus can be used with bone bolts or screws, or laminar or pedicle hooks. However, the rods are essentially straight which makes utilizing nonlinear points of connection on adjacent vertebrae difficult without the use of specially formed components.

An improved system and method to these early prior art systems and methods is disclosed in my U.S. Pat. Nos. 5,607,425, 5,716,357, 5,904,682, 6,010,504, 6,017,343, 6,336,927 and 6,379,354, the disclosures of which are included herein by reference. This system includes a plurality of link members that can be secured to adjacent vertebrae in chain-like fashion utilizing pedicle bolts or screws that are not collinear with each other. The link members can be used to subdivide multiple nonlinear pedicle fixation points into units of two adjacent points which two points can be interconnected with a single link member. This system thus facilitates multiple point fixation using two points at a time to overcome the problem in the prior art of nonalignment between plate openings and pedicle screws. The links form a chain and once they are secured to the pedicle screw or bolt with a locking nut, the result is a rigid construct securely affixed to the vertebrae.

The link members are in the form of plates or rods with opposite end portions and a central portion. The opposite end portions each have an aperture therein configured to receive attachment means affixed to the pedicle of adjacent vertebrae. The system also includes links in which the central portion is or is not offset. This offset provides increased vertebrae bone volume as compared with prior art apparatus which overlie the vertebra surface, which increases bone volume that can be used for bone grafts in fusions. In addition, the system permits visualization of bony maturation using radiographic studies since the links do not overlie the graft area.

The links can be used with and secured to vertebra pedicle screws, bolts, or pedicle or laminar hooks. A combination of hooks and screws or bolts can be used as well depending on the particular application.

The surface of the link member is preferably provided adjacent the apertures in the end portions thereof with radial cuts or other interdigitating structure for facilitating and enhancing the locking engagement of the links at a desired relative position. The bolt or hook has a threaded extension portion that cooperates with a locking nut to secure it to the link member, thereby securing the vertebra.

Transverse link members can be used to secure longitudinal chains to each other at their ends to form a quadrilateral frame having increased torsional stability.

While this system successfully addressed many of the problems found in earlier systems, it has been observed that this prior art system can be improved upon, especially in circumstances wherein new spinal conditions needing treatment arise after the original system has been implanted. For example, because the portion of the spine previously treated is rigidly fixed, a condition known as adjacent segment degeneration may develop in adjacent vertebrae. In order to extend the rigidly fixed treatment system by adding new link members, some or all of the locking nuts, transverse members and/or longitudinal linking members must be removed and disassembled to allow new linking members to be added. This dismantling is time-consuming and requires undesirable manipulation of the original linking system.

It is an object of this invention to provide an improved multi-link spinal treatment system wherein the addition of new links to extend a previously implanted multi-link system is easily accomplished without the need to excessively dismantle the previous system.

SUMMARY OF THE INVENTION

In brief summary, the invention in various embodiments is a multi-link spinal treatment assembly and method for addressing cervical, thoracic and lumbar spinal conditions comprising interconnected linking members and bone or pedicle fastener assemblies to receive the linking members, such as for example threaded bone or pedicle fasteners, end caps, and locknuts to secure the linking members to the bone or pedicals, whereby once the components are implanted and fixed, the multi-link system provides a rigid frame to preclude relative movement between vertebrae. The system may further comprise transverse linking members connecting two longitudinal linking members or linking member chain assemblies to each other at end points.

A typical bone or pedicle fastener comprises a threaded bone screw portion for insertion into the vertebra or pedicle and a threaded locknut receiving portion, the two threaded portions being separated by a radially extending flange or shoulder. The shoulder provides a stop or base to preclude movement of the end caps, linking members and locknuts in the distal direction along any axis. The bone fasteners may be structured such that the two threaded portions are coaxial or, in the case of poly-axial pedicle fasteners, the axes of the two threaded portions may not be coaxial. The fasteners may be structured to attach to the main vertebral body or to the vertebra pedicles.

The linking members are generally elongated members having a main body and two ends with circular apertures, with one or both of the apertures being slotted, i.e., partially open. The apertures are sized to allow passage therethrough of the threaded proximal portion of the bone fastener structured to receive the end caps, linking members and locknuts. The linking members are structured to be either longitudinal linking members aligned along the spinal axis or transverse linking members extending laterally across the spinal axis. Each apertured end will have a mating surface structured to mate or abut with the mating surface of an adjoining member of the multi-link assembly, such as another linking member or an end cap.

In most fixation scenarios adjacent vertebrae will be offset along an arc in the sagittal plane, the spine being curved rather than linear. Non-linear alignment can also be present in the coronal plane to account for this the main body of the longitudinal linking members is typically angled, curved, contoured or bent such that the mating surfaces of the apertured ends do not occupy the same or parallel planes. For the transverse linking members, the main body is also typically angled, curved, contoured or bent such that mating surfaces of the apertured ends do not occupy the same or parallel planes. The length and curvature of the linking members can be varied as necessary to account for variations in spines. In certain instances, the formation of a planar multi-link assembly rather than a curved multi-link assembly may be required, in which case the mating surfaces of the apertured ends may occupy the same or parallel planes.

In the preferred embodiment the longitudinal linking members are configured in a stepped manner, such that the first apertured end of a longitudinal linking member will be positioned above the second apertured end of a first adjoining longitudinal linking member when disposed on a pedicle or bone screw, and such that the second apertured end of the longitudinal linking member will be positioned below the first apertured end of a second adjoining longitudinal linking member. In this case the mating surface of the first apertured end will be on the opposite side from the mating surface of the second apertured end for a given longitudinal linking member. For a given transverse linking member, the mating surface of both apertured ends will be on the same side.

In an alternative embodiment the longitudinal linking members are configured in a non-stepped manner, such that the first apertured end of a longitudinal linking member will be positioned above the second apertured end of a first adjoining longitudinal linking member and the second apertured end of the longitudinal linking member will be positioned above the first apertured end of a second adjoining longitudinal linking member, or such that the first apertured end of a longitudinal linking member will be positioned below the second apertured end of a first adjoining longitudinal linking member and the second apertured end of the longitudinal linking member will be positioned below the first apertured end of a second adjoining longitudinal linking member. In this case the mating surface of the aperture ends of a given longitudinal linking member will be on the same side.

At least one apertured end of each longitudinal linking member is open or slotted to present a crescent-shaped end configuration, the slot being formed by a notch or open portion preferably encompassing the longitudinal axis of the linking member, while the other apertured end may be closed, i.e., in the form of a complete circle. For the transverse linking members, either both apertured ends are closed, i.e., fully circular, or both apertured ends are slotted, the slots being formed by a notch perpendicular to the longitudinal axis of the transverse linking member. In similar manner, some of the apertured end caps are fully closed while others are slotted.

The slots in the apertured ends of the linking members and the apertured end caps are sized such that the width of the slots is greater than the diameter of the locknut receiving portions, such that the linking members and slotted end caps can be removed from the locknut receiving portion of the bone fasteners in either a non-axial or axial direction. In other words, in contrast to linking members with closed ends, which can only be removed in the axial direction, the linking members and slotted end caps can be removed by movement in a direction perpendicular to the axis of the threaded locknut receiving portion of the bone fastener. Likewise, new linking members and slotted end caps can be positioned on the pedicle fasteners by movement in a direction perpendicular to the axis of the threaded locknut receiving portion of the pedicle or bone fastener.

A linked system or assembly is created by implanting two rows of bone fasteners along the spine and forming a longitudinally-extending chain assembly of longitudinal linking members on each row of bone fasteners, the bone fasteners having been inserted into the vertebral bodies or the pedicles as required. In the preferred embodiment the longitudinal linking members are aligned such that for adjoining linking members the slotted apertured end of one linking member is positioned below the closed end of the abutting linking member, the slotted apertured end abutting the bone fastener shoulder. For the end-most longitudinal linking members on one end of the linking member chains, a slotted end cap is positioned below the terminating closed end of each lining member, the slotted end cap abutting the bone fastener shoulder. For the other end of the linking member chains, a closed end cap is positioned above the slotted apertured end of the longitudinal linking members.

Alternatively, at either or both ends of the linking member chains a transverse linking member may be positioned between the linking member chains so as to extend between and connect the outermost apertured ends of the linking members. A transverse linking member having slotted apertured ends is positioned below the terminating closed ends of each linking member in the place of a slotted end cap, the slotted apertured ends of the transverse linking member abutting the bone fastener shoulder. A transverse linking member having closed apertured ends is positioned above the slotted apertured ends of the longitudinal linking members in the place of a closed end cap.

The linking members and the end caps are secured to the bone or pedicle fastener using locknuts, thereby creating a rigid framework fixing the vertebrae in a desired configuration. To extend a linking member chain assembly by adding new linking members to a previously implanted multi-link system, it is only necessary to loosen the locknuts covering the terminating ends of the endmost linking members a sufficient amount such that either the slotted end caps or a slotted transverse linking member can be slid from the bone or pedicle fasteners in the direction perpendicular to the bone fastener axis. The slotted apertured ends of new longitudinal linking members can then be slid non-axially onto the threaded proximal portions of each bone pedicle fastener above the shoulder and below the closed apertured ends of the previously implanted longitudinal linking members. The locknuts are then tightened to rigidly fix the multi-link assembly and corresponding vertebrae. Links may also be added by removing non-slotted end caps or non-slotted transverse linking members.

In alternative language, embodiments of the invention may be summarized and described as a multi-link spinal treatment system comprising: bone fasteners having a bone screw portion, a shoulder and a locknut receiving portion, the locknut receiving portion having a diameter and a bone fastener axis; longitudinal linking members, each of the longitudinal linking members comprising a main body having a longitudinal axis and two apertured ends having apertures sized to receive the locknut receiving portion therethrough, at least one of the apertured ends being a slotted apertured end comprising a slot having a width greater than the diameter of the locknut receiving portion; end caps, each of the end caps comprising an aperture sized to receive the locknut receiving portion therethrough, at least one of the end caps being a slotted end cap comprising a slot having a width greater than the diameter of the locknut receiving portion; and locknuts mounted onto the locknut receiving portions of the bone fasteners, the lock nuts securing the longitudinal linking members and the end caps against the shoulders of the bone fasteners; whereby after loosening but not removing one of the lock nuts from the bone fasteners, one of the slotted end caps is removable from the locknut receiving portion by movement in the direction perpendicular to the bone fastener axis, and further whereby the slotted apertured end of one of the longitudinal linking members is mountable onto the locknut receiving portion in place of the removed slotted end cap by movement in the direction perpendicular to the bone fastener axis. Further, the above further comprising one or more transverse linking members comprising a main body having a longitudinal axis and two apertured ends having apertures sized to receive the locknut receiving portion therethrough, at least one or more of the transverse linking members being a slotted transverse linking member wherein each of the apertured ends comprises a slot having a width greater than the diameter of the locknut receiving portion; wherein some of the locknuts mounted onto the locknut receiving portions of the bone fasteners secure the longitudinal linking members and the one or more transverse linking members against the shoulders of the bone fasteners; whereby after loosening but not removing two of the lock nuts from the bone fasteners, one of the slotted transverse linking members is removable from the locknut receiving portions by movement in the direction perpendicular to the bone fastener axis, and further whereby the slotted apertured end of one of the longitudinal linking members is mountable onto the locknut receiving portion in place of the removed transverse linking member by movement in the direction perpendicular to the bone fastener axis. Still further, the above further comprising non-slotted longitudinal linking members comprising a main body having a longitudinal axis and two apertured ends having apertures sized to receive the locknut receiving portion therethrough, wherein the apertured ends are not slotted; further comprising non-slotted longitudinal linking members comprising a main body having a longitudinal axis and two apertured ends having apertures sized to receive the locknut receiving portion therethrough, wherein the apertured ends are not slotted; wherein the slot of the apertured slotted end of the longitudinal linking member is oriented in the direction of the main body longitudinal axis of the longitudinal linking member; wherein each of the slots of the apertured ends of the slotted transverse linking member is oriented in the direction perpendicular to the main body longitudinal axis of the transverse linking member; wherein the longitudinal linking member main bodies are non-planar; and/or wherein the longitudinal linking member main bodies are stepped; wherein the apertured ends of the longitudinal linking members and the apertured ends of the end caps comprise mating surfaces, the mating surfaces comprising anti-rotation structures.

In alternative language, embodiments of the invention may be summarized and described as a method of treating spinal conditions comprising the steps of: providing the multi-link spinal system as described above; implanting the bone screw portions of the bone fasteners into vertebrae; forming a chain of longitudinal linking members by mounting longitudinal linking members in overlapping manner onto adjacent bone fasteners such that the locknut receiving portions of the bone fasteners extend through the apertured ends of the longitudinal linking members; installing locknuts onto the locknut receiving portions of the bone fasteners having overlapping longitudinal members; installing end caps either above or below the longitudinal linking members onto the locknut receiving portions of the bone fasteners not having overlapping longitudinal members, wherein at least one of the end caps is a slotted end cap; and installing locknuts onto the locknut receiving portions of the bone fasteners having end caps. Further, the above further comprising the steps of: implanting the bone screw portions of one or more additional bone fasteners into vertebrae; loosening but not removing one or more of the locknuts installed on the locknut receiving portions of the bone fasteners retaining slotted end caps; removing one or more of the slotted end caps from the locknut receiving portions of the bone fasteners by movement in the direction perpendicular to the bone fastener axis; inserting the slotted apertured ends of one or more of the longitudinal linking members onto the locknut receiving portions of the bone fasteners in place of the removed slotted end caps by movement in the direction perpendicular to the bone fastener axis, and mounting the one or more longitudinal linking members on the one or more additional bone fasteners; tightening the loosened one or more locknuts. Still further, the above further comprising the steps of: providing the multi-link spinal system of above; implanting the bone screw portions of the bone fasteners into vertebrae; forming a chain of longitudinal linking members by mounting longitudinal linking members in overlapping manner onto adjacent bone fasteners such that the locknut receiving portions of the bone fasteners extend through the apertured ends of the longitudinal linking members; installing locknuts onto the locknut receiving portions of the bone fasteners having overlapping longitudinal members; and installing transverse linking members either above or below the longitudinal linking members onto the locknut receiving portions of the bone fasteners not having overlapping longitudinal members, wherein at least one of the transverse linking members is a slotted transverse linking member; installing locknuts onto the locknut receiving portions of the bone fasteners having transverse linking members. Further, implanting the bone screw portions of one or more additional bone fasteners into vertebrae; loosening but not removing the locknuts installed on the locknut receiving portions of the bone fasteners retaining one of the slotted transverse linking members; removing the slotted transverse linking member from the locknut receiving portions of the bone fasteners by movement in the direction perpendicular to the bone fastener axis; inserting the slotted apertured ends of one or more of the longitudinal linking members onto the locknut receiving portions of the bone fasteners in place of the removed slotted transverse linking members by movement in the direction perpendicular to the bone fastener axis, and mounting the one or more longitudinal linking members on the one or more additional bone fasteners; tightening the loosened one or more locknuts.

Alternatively, embodiments of the invention may be summarized and described as a method of treating spinal conditions comprising the steps of: providing the multi-link spinal system above; implanting the bone screw portions of the bone fasteners into vertebrae; forming a chain of longitudinal linking members by mounting longitudinal linking members in overlapping manner onto adjacent bone fasteners such that the locknut receiving portions of the bone fasteners extend through the apertured ends of the longitudinal linking members; installing locknuts onto the locknut receiving portions of the bone fasteners having overlapping longitudinal members; and installing either end caps or transverse linking members either above or below the longitudinal linking members onto the locknut receiving portions of the bone fasteners not having overlapping longitudinal members, wherein at least one of the end caps is a slotted end cap or at least one of the transverse linking members is a slotted transverse linking member; installing locknuts onto the locknut receiving portions of the bone fasteners having end caps or transverse linking members. Further, the above further comprising the steps of: implanting the bone screw portions of one or more additional bone fasteners into vertebrae; loosening but not removing the locknuts installed on the locknut receiving portions of the bone fasteners retaining the at least one slotted end cap or the at least one slotted transverse linking members; removing the at least one slotted end cap or the at least one slotted transverse linking member from the locknut receiving portions of the bone fasteners by movement in the direction perpendicular to the bone fastener axis; inserting the slotted apertured ends of one or more of the longitudinal linking members onto the locknut receiving portions of the bone fasteners in place of the removed at least one slotted end cap or the at least one slotted transverse linking member by movement in the direction perpendicular to the bone fastener axis, and mounting the one or more longitudinal linking members on the one or more additional bone fasteners; tightening the loosened one or more locknuts.

DETAILED DESCRIPTION OF THE INVENTION

Figure 1:
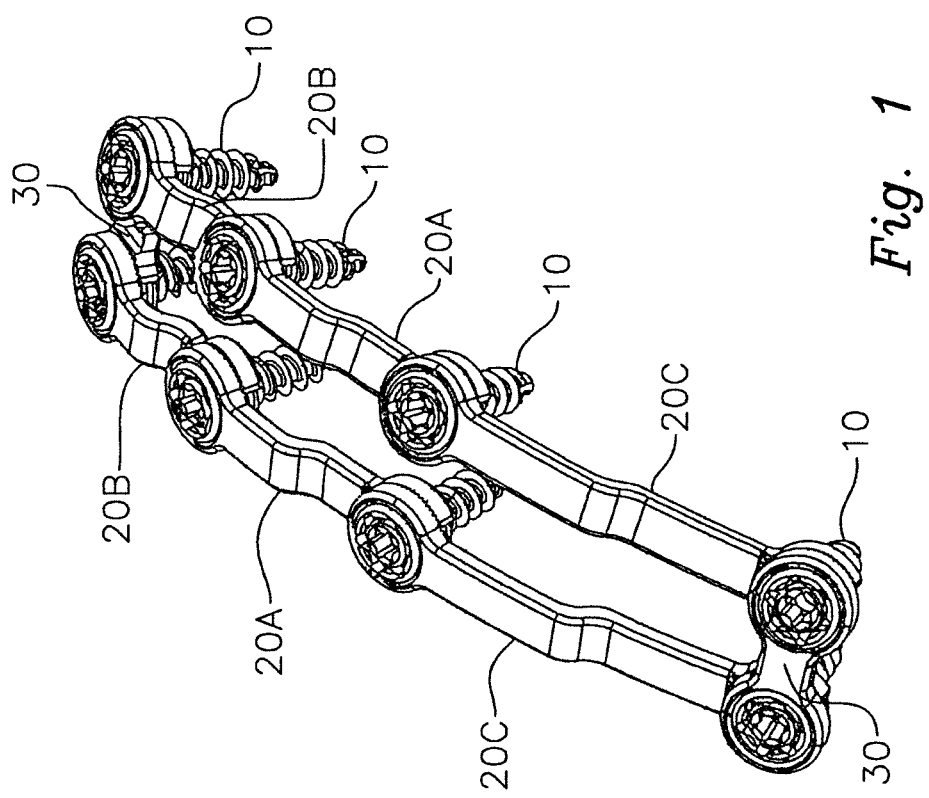
FIGS. 1-6 illustrate a representative linking member chain assembly.

In general, the invention is in various embodiments a multi-link spinal treatment system or assembly and method for addressing cervical, thoracic and lumbar spinal conditions comprising interconnected linking members 20, bone or pedicle fastener assemblies to receive the linking members 20, such as for example threaded bone or pedicle fasteners or screws 10 (referred to herein collectively as bone fasteners 10), end caps 50/60 to provide proper spacing and security on the pedicle fastener axis, and locknuts 14 to secure the linking members 20 to the bone fasteners 10, whereby once the components are implanted and fixed, the multi-link system provides a rigid frame to preclude relative movement between vertebrae. The system may further comprise transverse linking members 30/40 connecting two linking members 20 or two linking member chain assemblies 90 to each other at various points.

As used herein, the terms distal, lower, bottom or the like shall refer to the direction toward the spine when the multi-link spinal treatment assembly is implanted on the spine. The terms proximal, upper, top or the like shall refer to the opposite direction, i.e., the direction away from the spine when the multi-link spinal treatment assembly is implanted on the spine. The multi-link assembly may be disposed on the anterior or dorsal, volar or posterior side of the spine, and may be disposed on the cervical thoracic or lumbar vertebrae.

Figure 26:
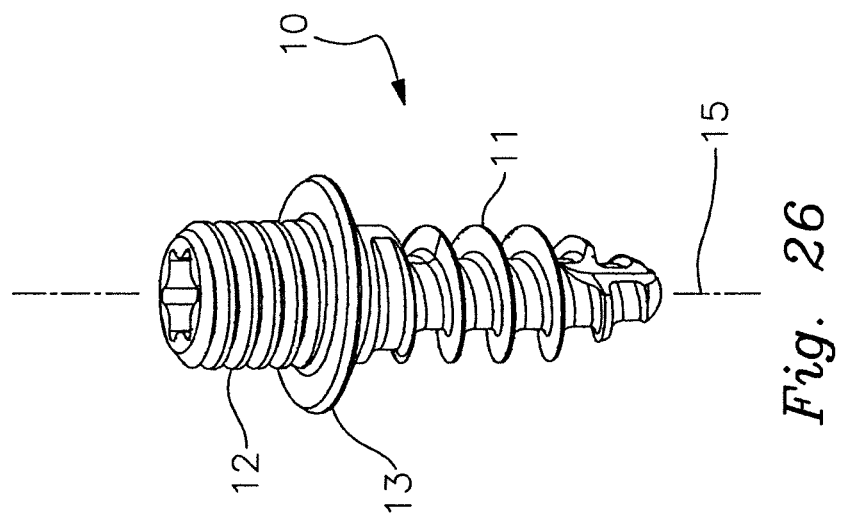
FIG. 26 illustrates a representative bone or pedicle fastener.
Figure 27:
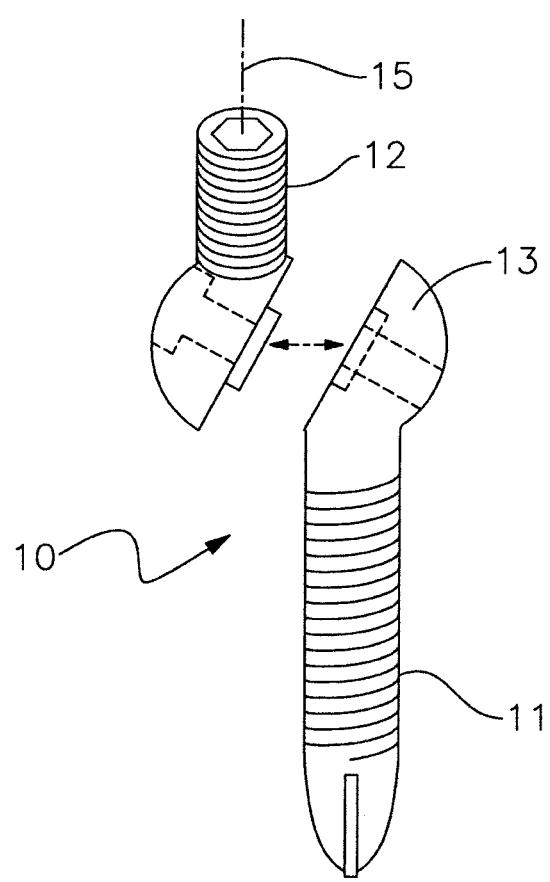
FIG. 27 illustrates a representative multi-directional bone or pedicle fastener.
Figure 1:
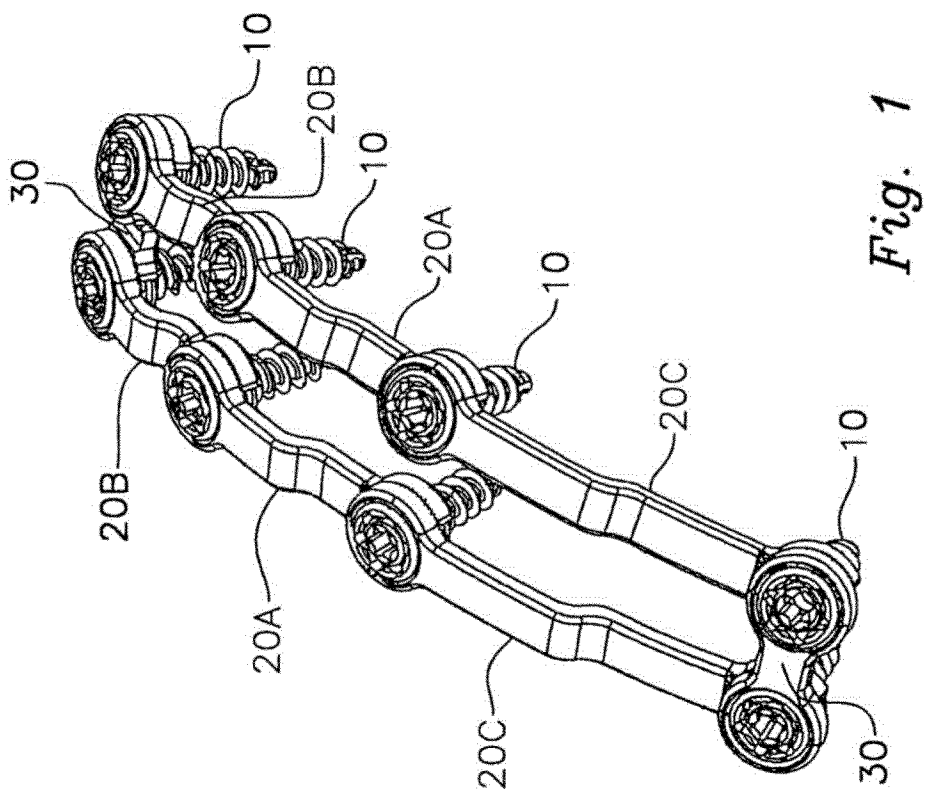
Figure 2:
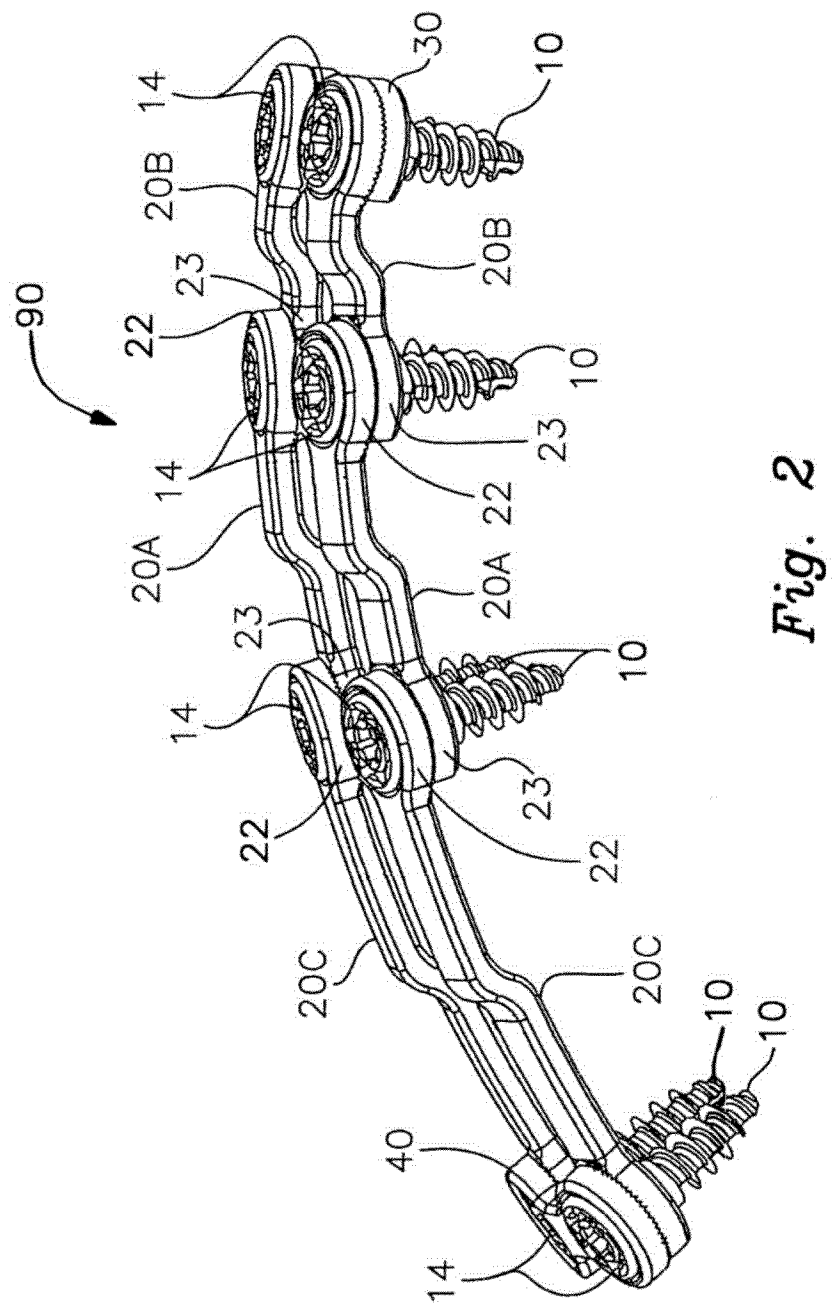
Figure 3:
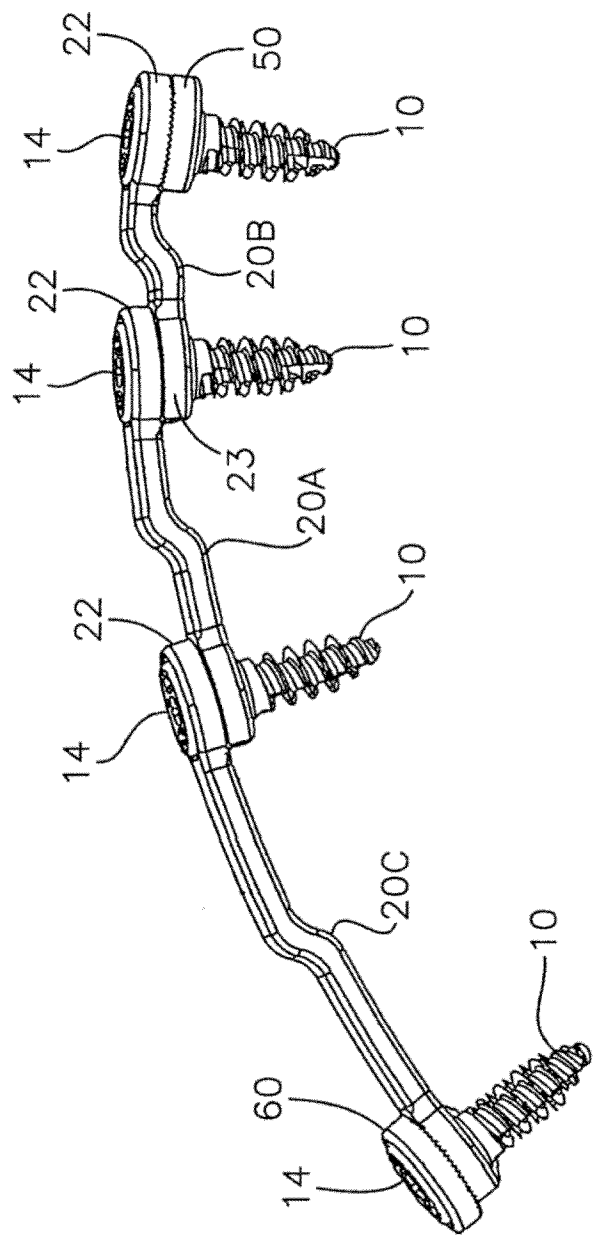
Figure 4:
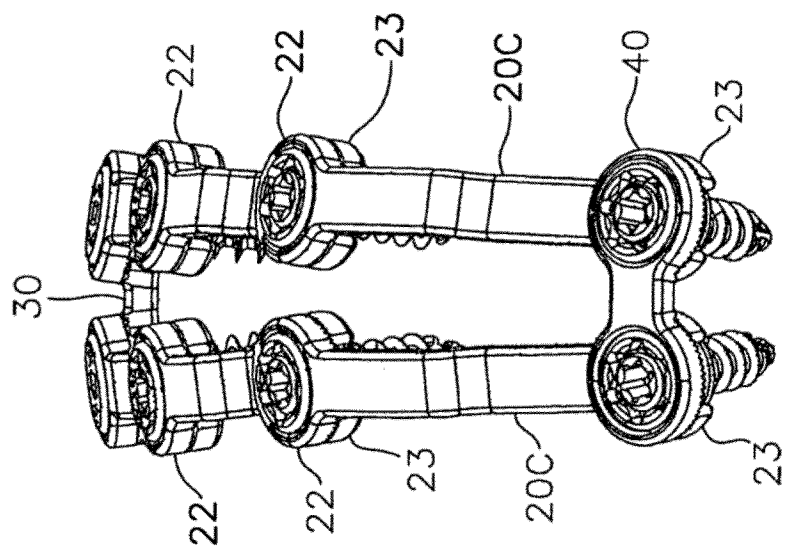
Figure 5:
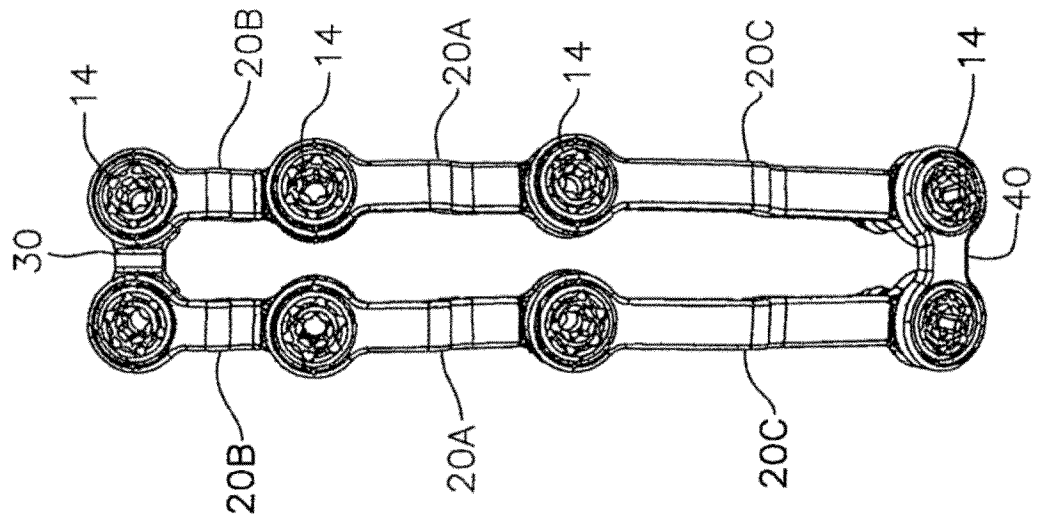
Figure 6:
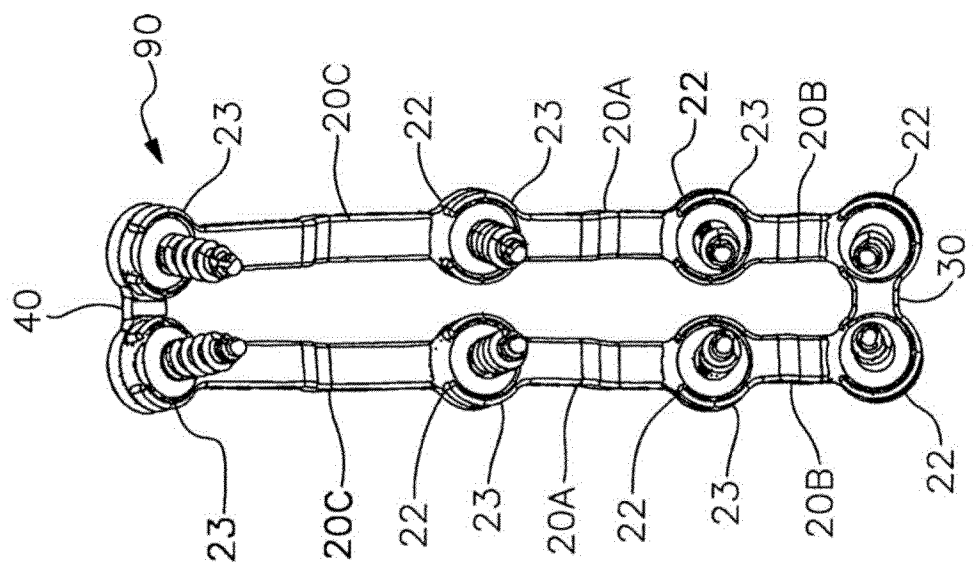
Figure 7:
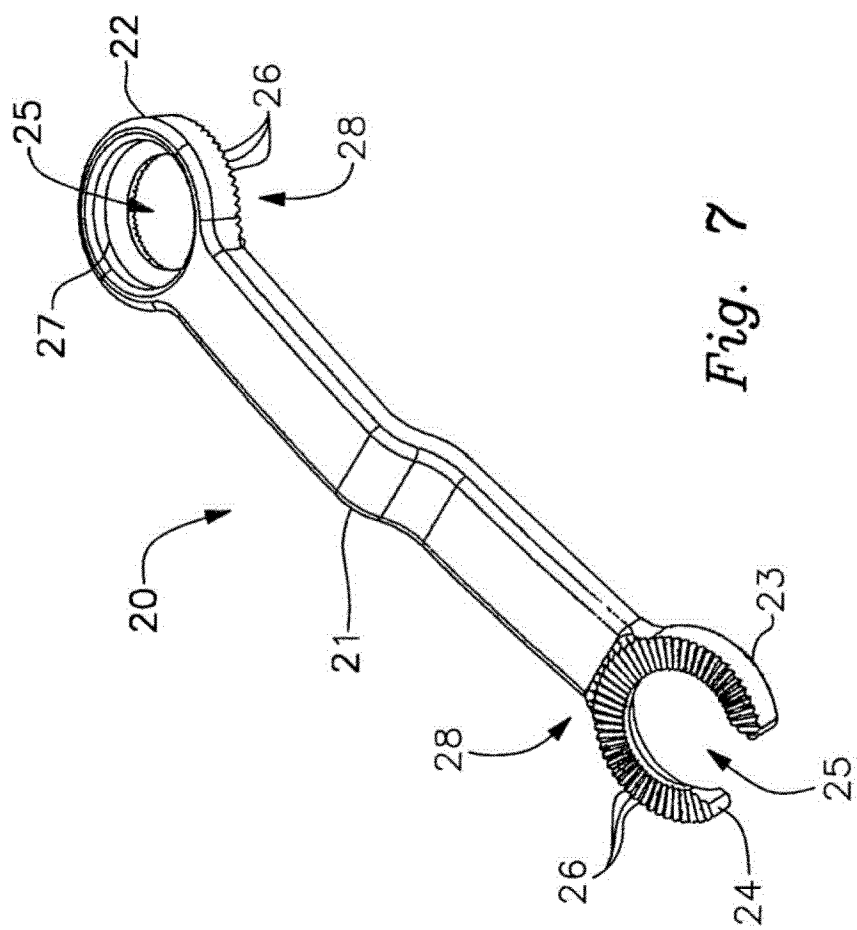
Figure 8:
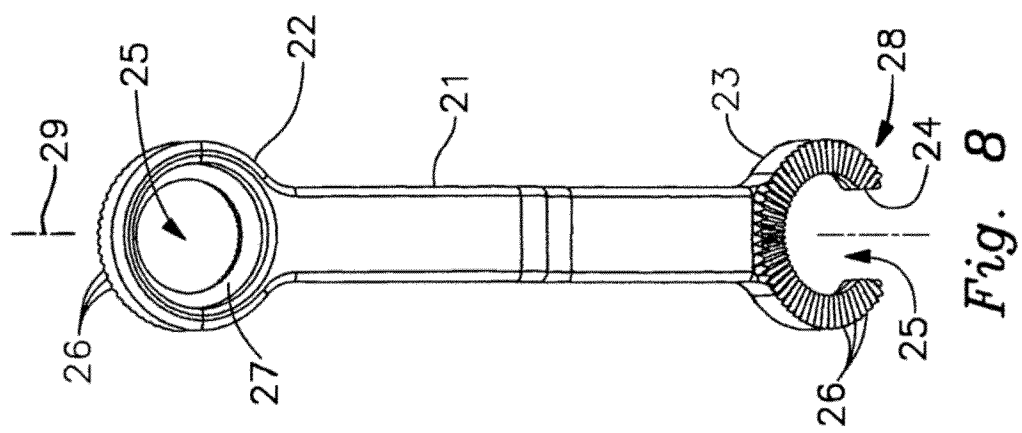
Figure 10:
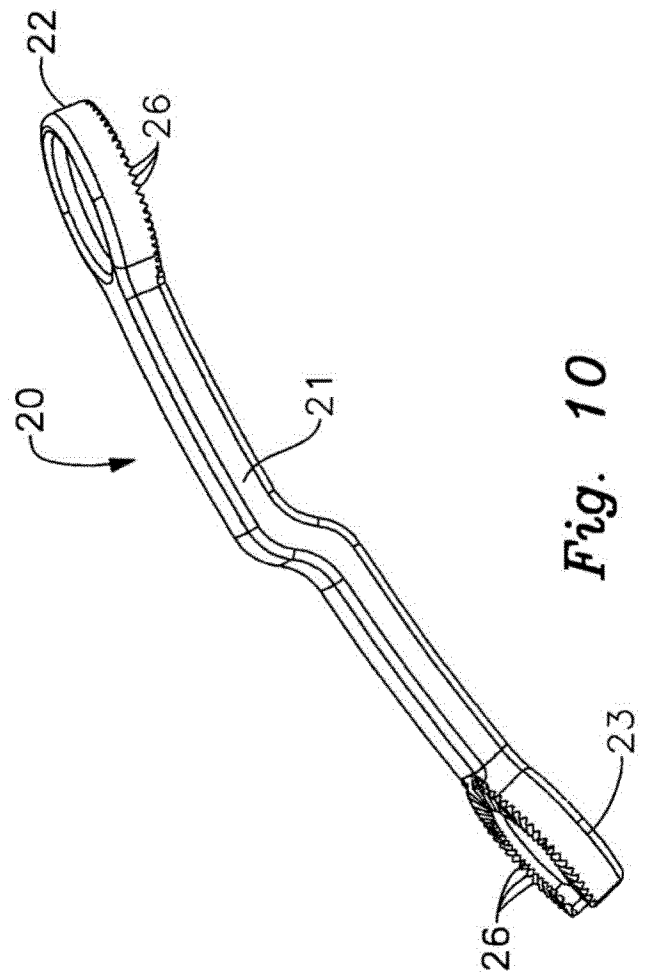
Figure 11:
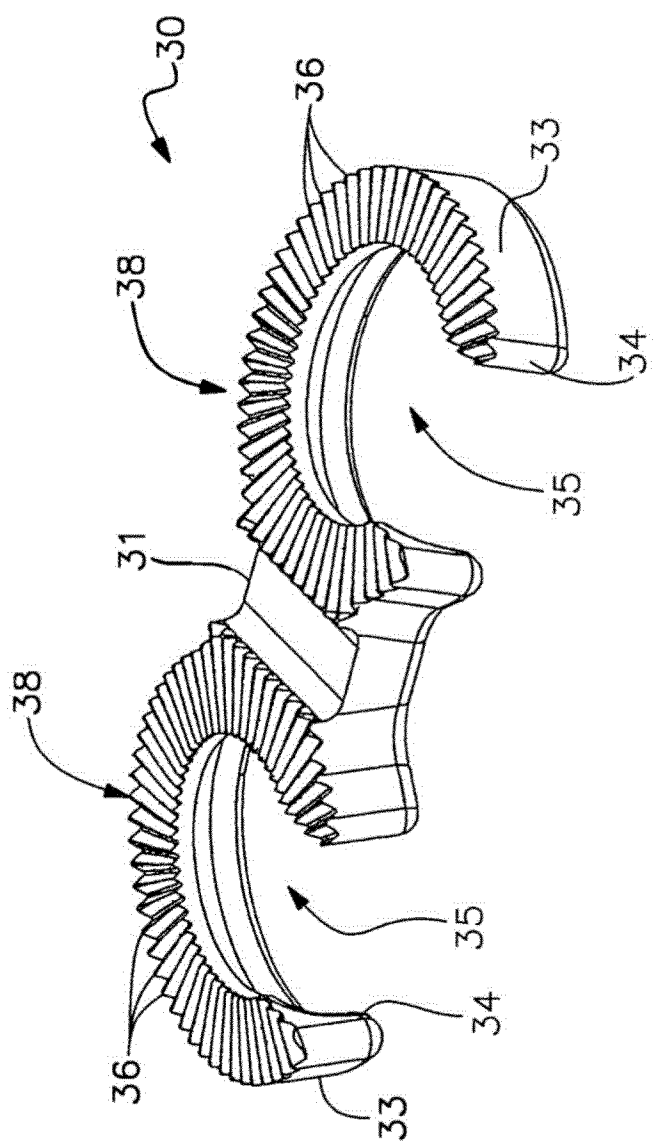
Figure 14:
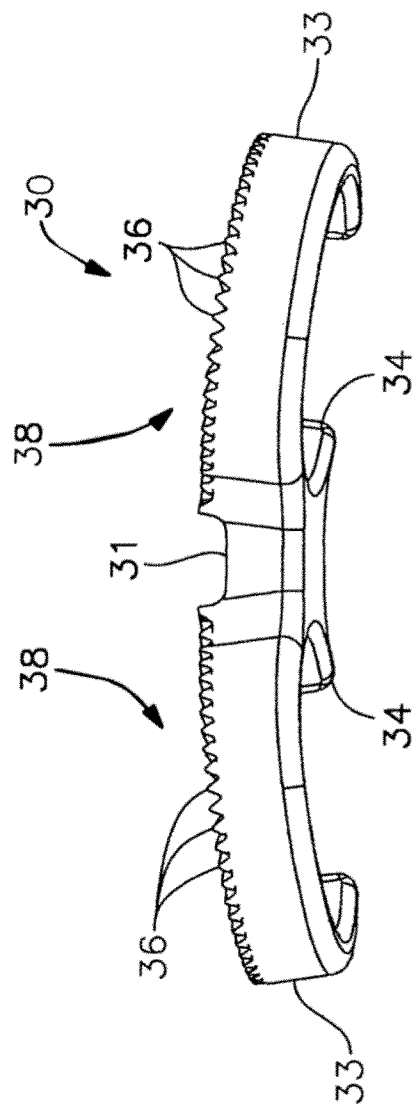
Figure 15:
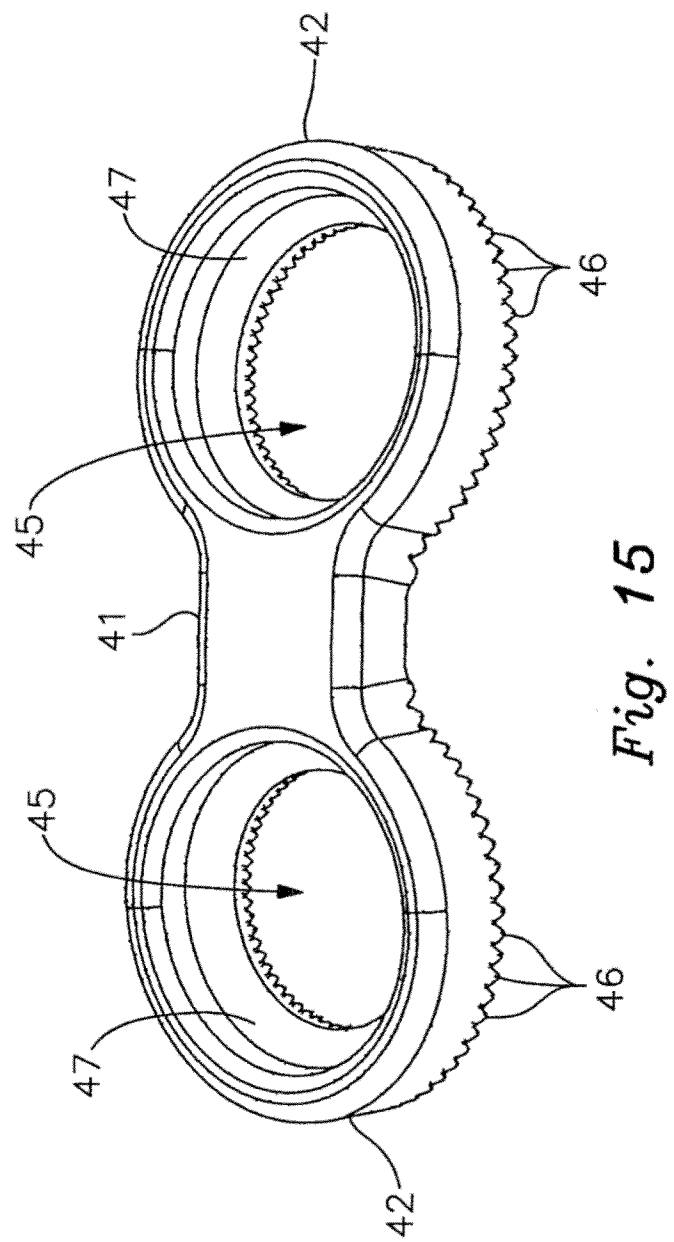
Figure 16:
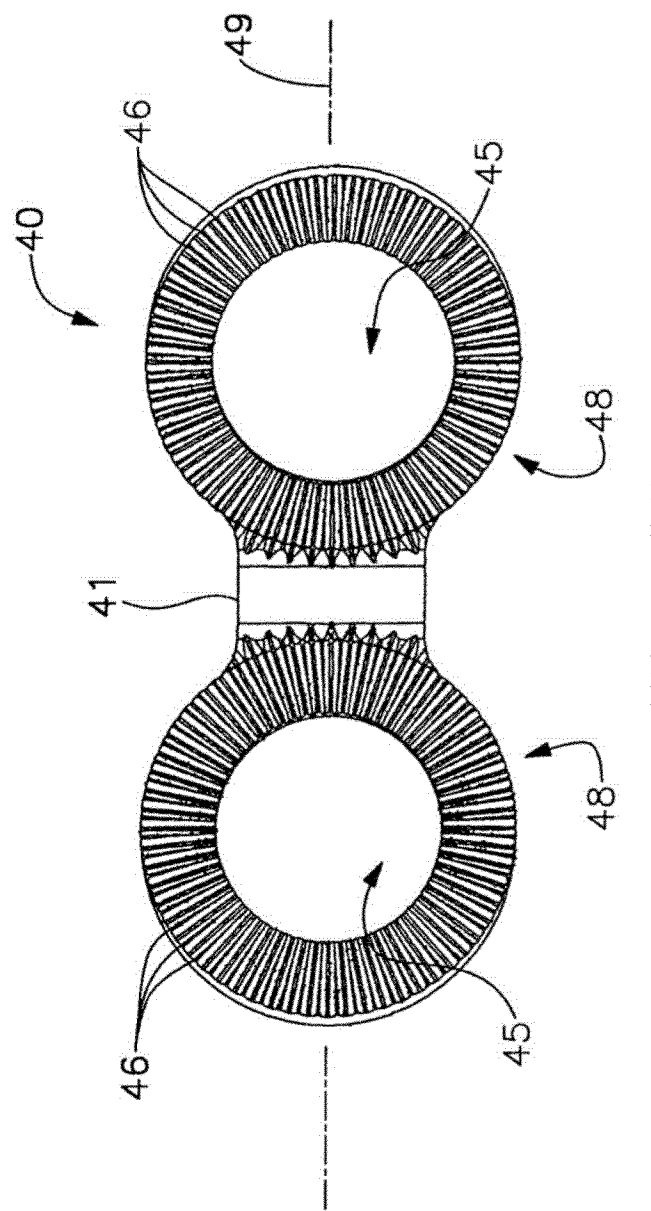
Figure 17:
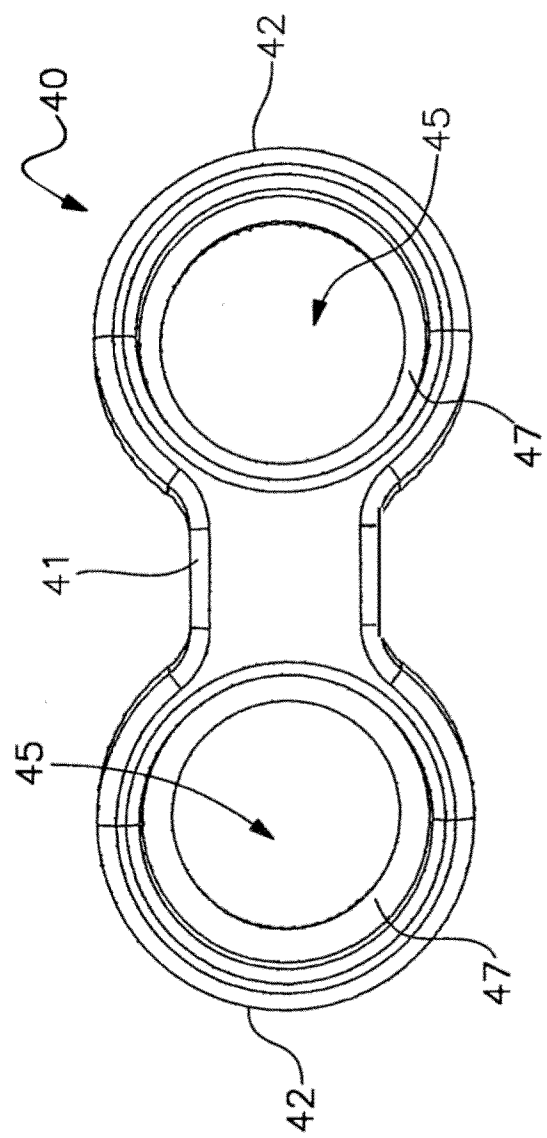
Figure 18:
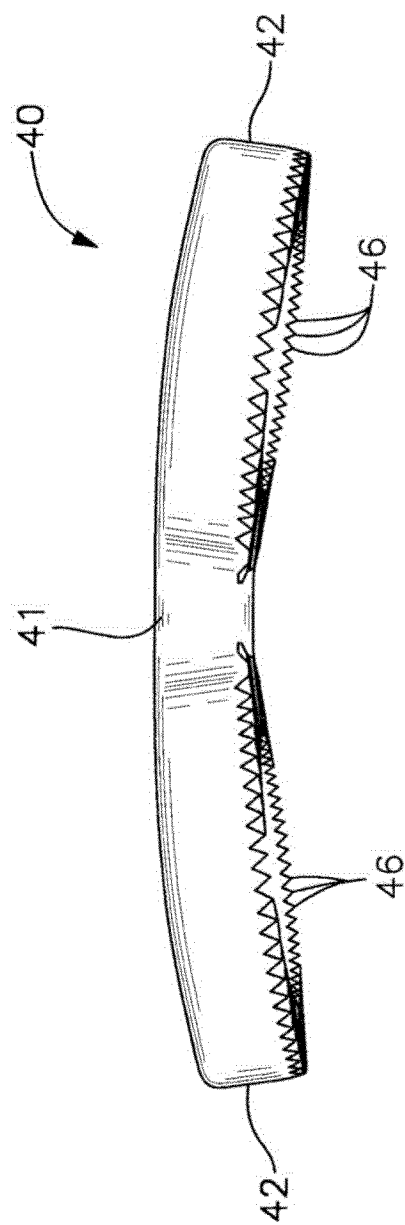
Figure 20:
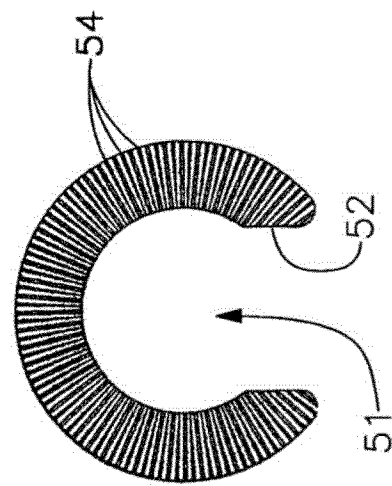
Figure 19:
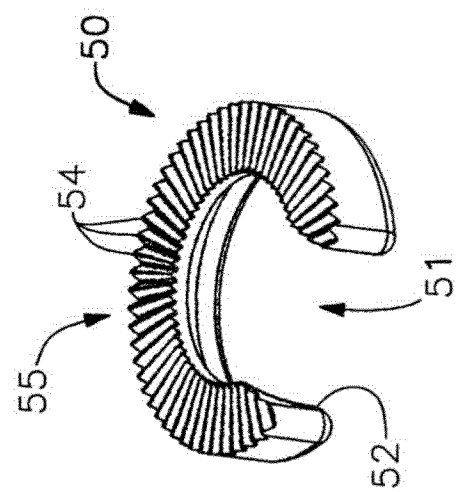
Figure 22:
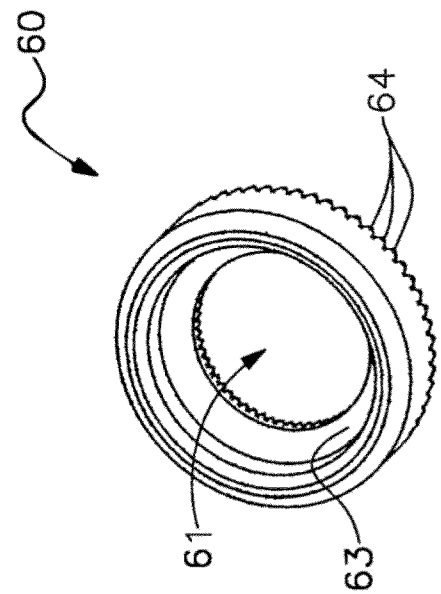
Figure 21:
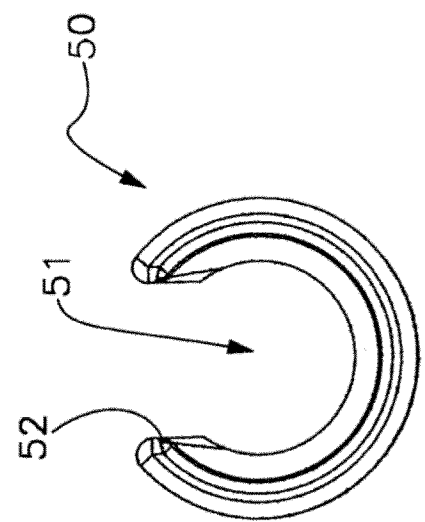
Figure 24:
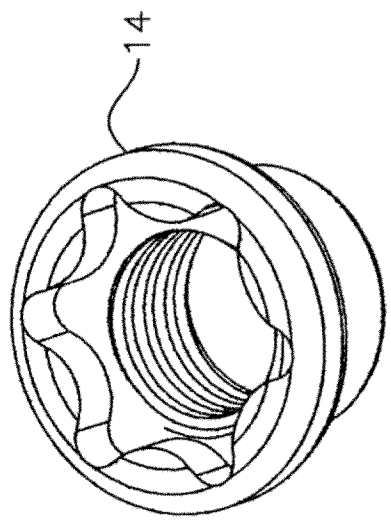
Figure 23:
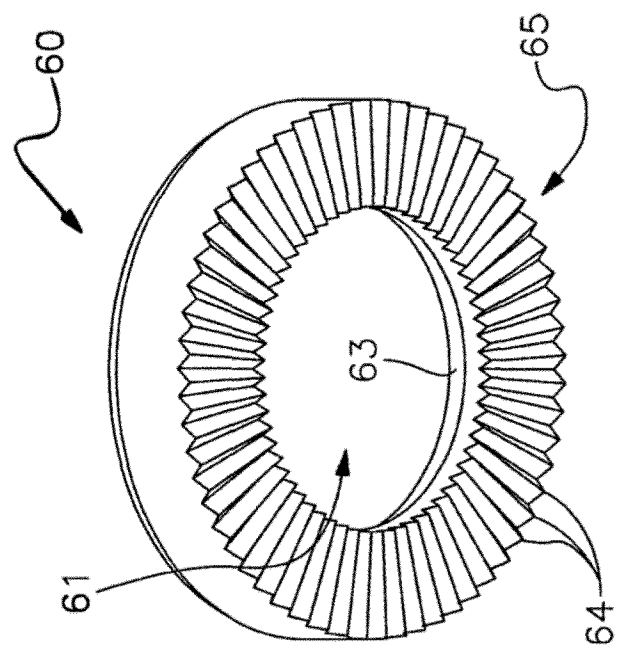
Figure 26:
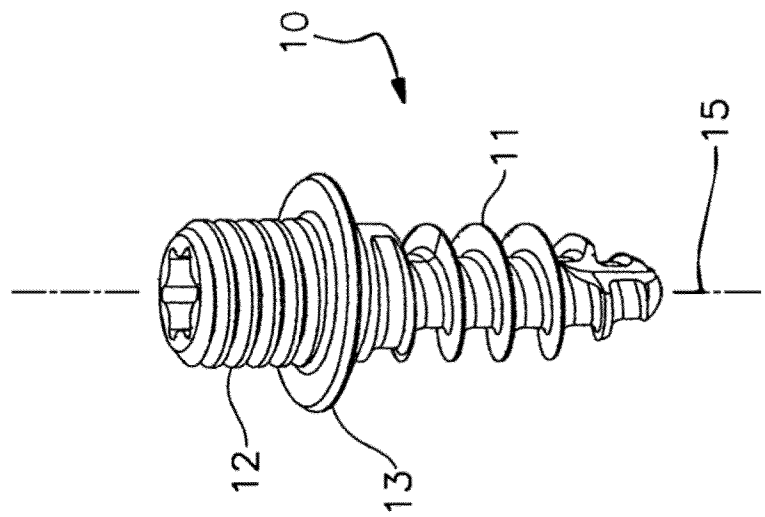
Figure 25:
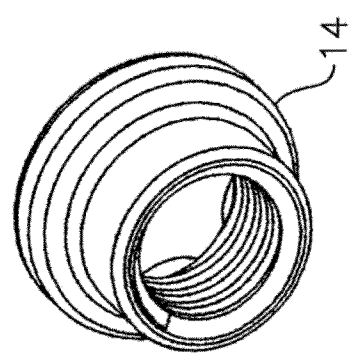
Figure 27:
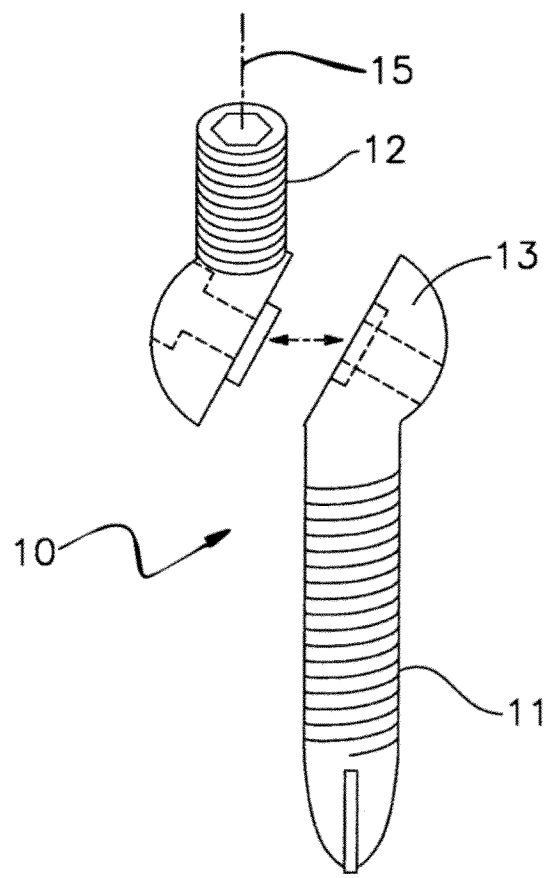

As illustrated in FIG. 26, a typical bone fastener 10 comprises a threaded, distal, bone screw portion 11 structured for insertion into bone material, either the vertebral body or the pedicle, and a threaded, proximal, locknut receiving portion 12 having a defined diameter, the two threaded portions 11/12 being separated by a radially extending flange or shoulder 13. For a rigid fastener 10, the two threaded portions 11/12 are coaxial. In the case of poly-axial bone fasteners 10, as shown in FIG. 27, a split body enables the axes of the two threaded portions 11/12 to be oriented so as to not be coaxial. The split body is the shoulder 13 providing a stop or base to preclude movement of the end caps 50/60, linking members 20/30/40 and locknuts 14 in the distal direction along the axis 15 of the threaded locknut receiving portion 12 of the bone fastener 10. Both types of bone fasteners 10 are well known.

The longitudinal linking members 20, in the preferred embodiment as shown in FIGS. 7-10, are generally elongated members having a main body or connecting segment 21 and two terminal ends 22/23 with circular apertures 25 sized to allow passage therethrough of the threaded proximal portion 12 of the bone fastener 10. The longitudinal linking members 20 are configured in a stepped manner and are structured to be aligned end-to-end along the spinal axis to form linking member chain assemblies 90, as shown in FIGS. 1-6, such that the first apertured end 22 of a longitudinal linking member 20A will be positioned above the second apertured end 23 of a first adjoining longitudinal linking member 20B when disposed on a bone fastener 10, and such that the second apertured end 23 of the longitudinal linking member 20A will be positioned below the first apertured end 22 of a second adjoining longitudinal linking member 20C. In this case the mating surface 28 of the first apertured end 22 will be on the opposite side from the mating surface 28 of the second apertured end 23 for a given longitudinal linking member 20.

Each apertured end 22/23 has a mating surface 28, the mating surfaces 28 on a longitudinal linking member 20 being disposed on opposite sides. For the longitudinal linking members 20, the main body 21 is angled, curved, contoured or bent such that the mating surfaces 28 of the apertured ends 22/23 occupy the desired arc for proper fixation of the adjoining vertebrae. At least one longitudinal linking member 20 has an apertured end 23 that is slotted so as to present a crescent-shaped configuration, the slot 24 being formed by a notch or gapped segment, preferably extending along or encompassing the longitudinal axis 29 of the linking member 20, while the other apertured end 22 is closed, i.e., in the form of a complete circle having no notch or gap. Alternatively, both aperture ends 22 and 23 may be slotted. The width of the slot 24 is greater than the diameter of the locknut receiving portion 12 of the bone fastener 10.

The upper surface of the slotted apertured end 23 defines the mating surface 28 for this end and the lower surface of the closed apertured end 22 defines the mating surface 28 for the opposite end. Most preferably the mating surfaces 28 are provided with anti-rotation physical features or structures 26, such as ridges, teeth, serrations, scoring or the like, which inhibit or preclude relative rotation through friction or mechanical mating. Also preferably, the upper surface of the closed apertured end 22 is provided with a beveled recess 27 surrounding the aperture 25, the beveled recess 27 sized and configured to receive the lower portion of the locknut 14 in order to reduce the overall profile of the system.

In an alternative embodiment (not shown) the longitudinal linking members 20 are configured in a non-stepped manner, such that the first apertured end 22 of a longitudinal linking member 20A will be positioned above the second apertured end 23 of a first adjoining longitudinal linking member 20B and the second apertured end 23 of the longitudinal linking member 20A will be positioned above the first apertured end 22 of a second adjoining longitudinal linking member 20C, or such that the first apertured end 22 of a longitudinal linking member 20A will be positioned below the second apertured end 23 of a first adjoining longitudinal linking member 20B and the second apertured end 23 of the longitudinal linking member 20A will be positioned below the first apertured end 22 of a second adjoining longitudinal linking member 20C. In this case the mating surface 28 of the apertured ends of a given longitudinal linking member 20 will be on the same side.

Figure 22:
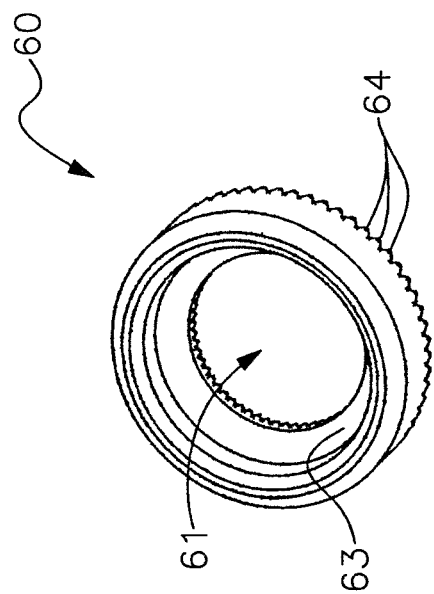
FIGS. 22-23 illustrate a representative closed end cap member.
Figure 21:
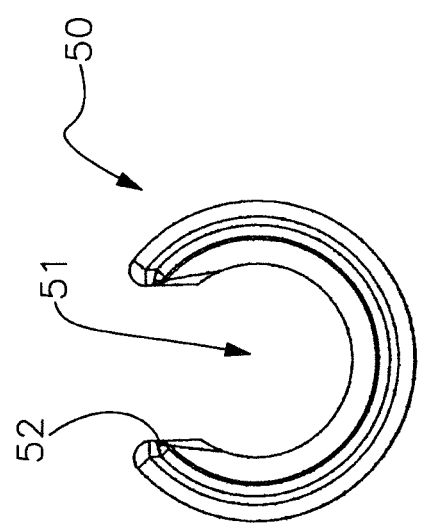
Figure 23:
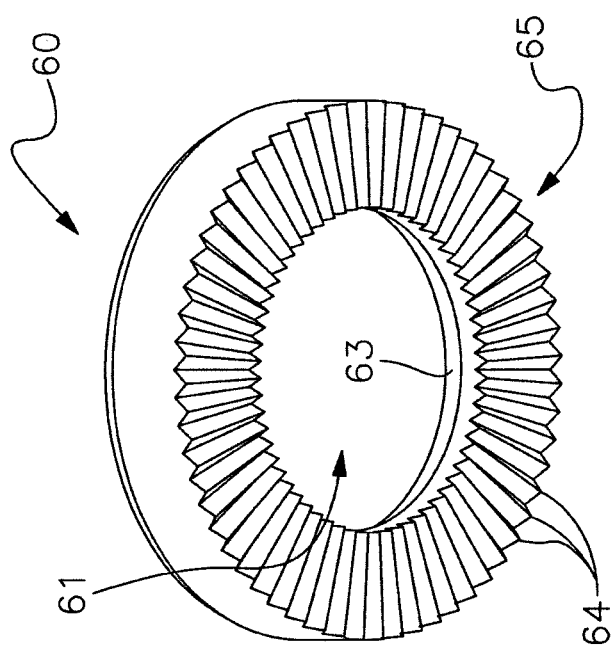

The end caps 50/60, shown in FIGS. 19-23, are members that are preferably generally circular in configuration with a central circular aperture 51/61. Each slotted apertured end cap 50 is provided with a slot 52 so as to be crescent-shaped (FIGS. 19-21), while closed apertured end caps 60 are fully circular with no slots (FIGS. 22-23). The width of the slot 52 is greater than the diameter of the locknut receiving portion 12 of the bone fastener 10. For the slotted end caps 50, the upper surface defines the mating surface 55 and is preferably provided with anti-rotation structures 54, as this end cap 50 will be positioned beneath the closed apertured end 22 and abutting the mating surface 28 and anti-rotation structure 26 of the longitudinal linking member 20. For the closed end caps 60, the lower surface defines the mating surface 65 and is preferably provided with anti-rotation structures 64, as this end cap 60 will be positioned above the slotted apertured end 23 and abutting the mating surface 28 and anti-rotation structure 26 of the longitudinal linking member 20. Also preferably, the upper surface of the end cap 60 is provided with a beveled recess 63 surrounding the aperture 61, the beveled recess 63 sized and configured to receive the lower portion of the locknut 14 to reduce the overall profile of the system.

The slots 24 in the apertured ends 23 of the longitudinal linking members 20 and the slotted end caps 50 are sized such that the linking members 20 and slotted end caps 50 can be non-axially removed from the locknut receiving portion 12 of the bone fasteners 10. In other words, the linking members 20 and slotted end caps 50 can be removed by movement in the direction perpendicular to the central axis 15 of the locknut receiving portion 12 of the bone fastener 10. Likewise, as explained in detail below, when it is desirable to extend the linking member chain assemblies 90, new longitudinal linking members 20 and slotted end caps 50 can be positioned onto bone fasteners 10 by movement in the direction perpendicular to the central axis 15 of the locknut receiving portion 12 of the bone fastener 10.

A linked system or assembly is created by implanting two rows of pedicle fasteners 10 along the spine and forming a longitudinally-extending chain 90 of longitudinal linking members 20 on each row of bone fasteners 10, as shown in FIGS. 1-6. The longitudinal linking members 20 are aligned such that for adjoining linking members 20 the slotted apertured end 23 of one linking member 20 is positioned below the closed apertured end 22 of the abutting linking member 20, the slotted apertured end 23 abutting the pedicle fastener shoulder 13. For the end-most longitudinal linking members 20 on one end of the linking member chains 90, a slotted end cap 50 is positioned below the terminating closed end 22 of each linking member 20, the slotted end cap 50 abutting the pedicle fastener shoulder 13. For the other terminating ends of the linking member chains 90, a closed end cap 60 is positioned proximally above the slotted apertured end 23 of the longitudinal linking members 20.

Alternatively, at either or both ends of the linking member chains 90 a transverse linking member 30/40 may be positioned between the linking member chains 90 so as to extend between and connect the outermost apertured ends 22/23 of the longitudinal linking members 20. The transverse linking members 30/40 each comprise a main body or connecting segment 31/41 with terminal ends 33/42, each end 33/42 having a circular aperture 35. For certain transverse linking members 40 (FIGS. 15-18) both apertured ends 42 are closed, i.e., fully circular, while for other transverse linking members 30 (FIGS. 11-14) both apertured ends 33 are slotted, i.e., crescent-shaped, the slots 34 being formed by a slot, notch or open segment oriented perpendicularly to the longitudinal axis 39 of the transverse linking member 30. The width of the slot 34 is greater than the diameter of the locknut receiving portion 12 of the bone fastener 10. In practice, the pair of linking member chains 90 will not occupy the same plane as they will each be disposed substantially perpendicularly to the spinal axis, and therefore the main bodies 31/41 will be angled, curved, contoured or bent such that the apertured ends 33/42 face toward each other slightly. For a given transverse linking member 30/40, the mating surfaces 38/48 of both apertured ends 33/42 will be on the same side.

To increase the rigidity of the linking system, a transverse linking member 30 having slotted apertured ends 33 may be positioned below the terminating closed ends 22 of the linking members 20 in the place of a slotted end cap 50, the slotted apertured ends 33 of the transverse linking member 30 abutting the pedicle fastener shoulder 13. A transverse linking member 40 having closed apertured ends 42 may be positioned above the slotted apertured ends 23 of the longitudinal linking members 20 in the place of a closed end cap 40B.

Preferably, the upper surfaces of the apertured ends 33 of the transverse linking member 30 define a mating surface 38 provided with anti-rotation structures 36, as the anti-rotation structures 36 will abut the anti-rotation structures 26 of the closed aperture ends 22 of the longitudinal linking member 20. Preferably, the lower surfaces of the closed apertured ends 42 of the transverse linking member 40 define a mating surface 48 provided with anti-rotation structures 46, as the anti-rotation structures 46 will abut the anti-rotation structures 26 of the slotted apertured ends 23 of the longitudinal linking members 20. It is also preferable that the upper surfaces of the transverse linking member 40 be provided with a beveled recess 47 adapted to receive the bottom portion of the locknuts 14.

Figure 24:
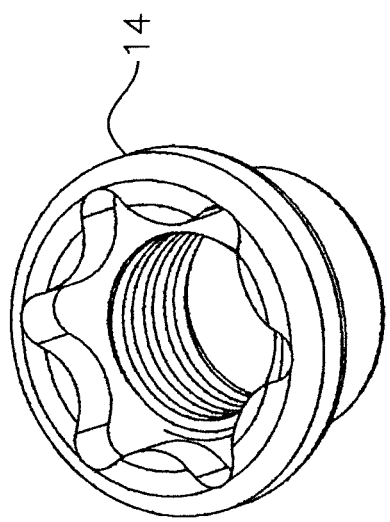
FIGS. 24-25 illustrate a representative locking nut.
Figure 25:
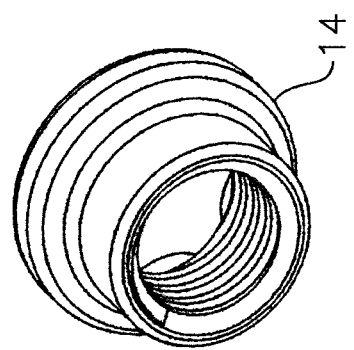

The longitudinal linking members 20, the transverse linking members 30/40 if present, and the end caps 50/60 if present are secured to the bone fasteners 10 using locknuts 14 (FIGS. 24-25), the locknuts 14 being tightened onto the proximal locknut receiving portion 12 of the bone fasteners 10 to create a rigid framework fixing the vertebrae in a desired configuration. To add new longitudinal linking members 20 to either end of a previously implanted multi-link system, additional bone fasteners 10 are implanted into the vertebrae. The locknuts 14 covering the terminating closed ends 22 of the endmost linking members 20 are then loosened a sufficient amount to release the pressure such that the slotted end caps 50 or a slotted transverse linking member 30 can be slid off of the bone fasteners 10 in the direction perpendicular to the pedicle fastener axis 15. The slotted apertured ends 23 of new longitudinal linking members 20 are then slid laterally onto the exposed threaded proximal portions 12 of each bone fastener 10 above the shoulder 13 and below the closed apertured ends 22 of the previously implanted longitudinal linking members 20. The locknuts 14 are then tightened to rigidly fix the multi-link assembly and corresponding vertebrae. To add new longitudinal linking members 20 to the opposite end of a previously implanted multi-link system, the locknuts 14 covering the closed endcaps 60 or a closed transverse linking member 40 are removed from the bone fasteners 10. The closed endcaps 60 or the closed transverse linking member 40 are also removed from the bone fasteners 10. The closed apertured ends 22 of new longitudinal linking members 20 are then axially positioned onto the locknut receiving portions 12 of the bone fasteners 10 and secured with the locknuts 14.

It is contemplated and understood that equivalents and substitutions for certain elements described above may be obvious to those of skill in the art, and therefore the true scope and definition of the invention is to be as set forth in the following claims.

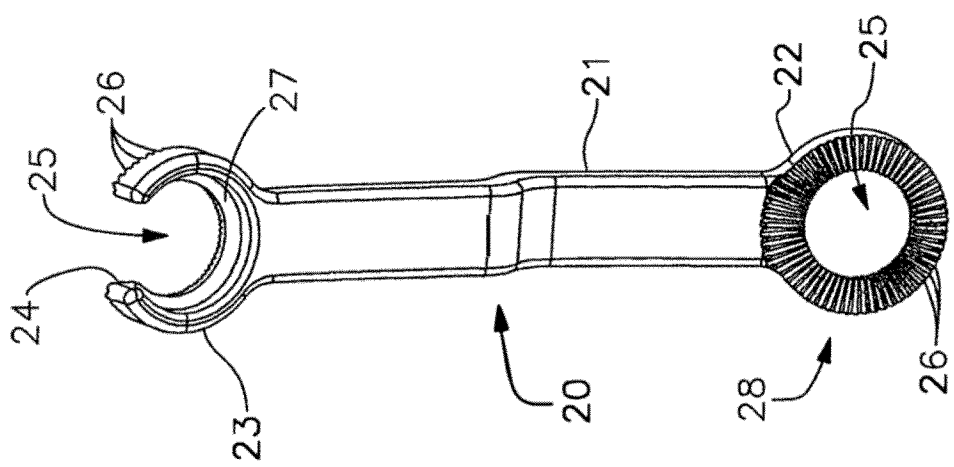

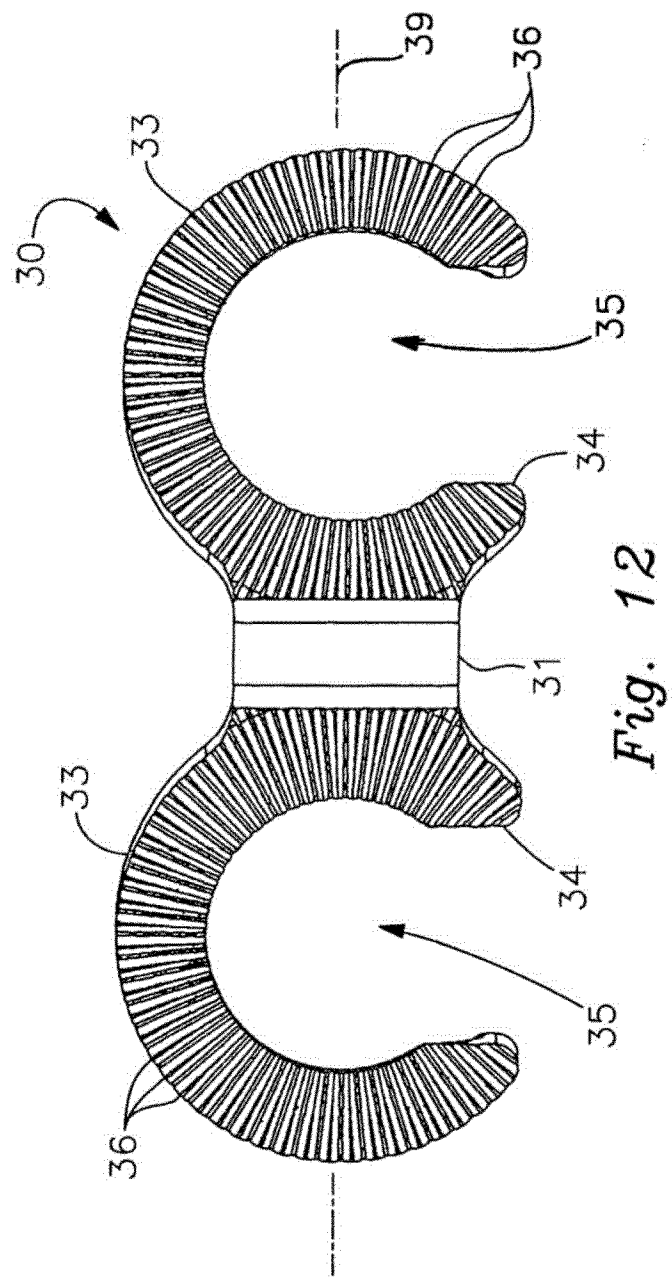

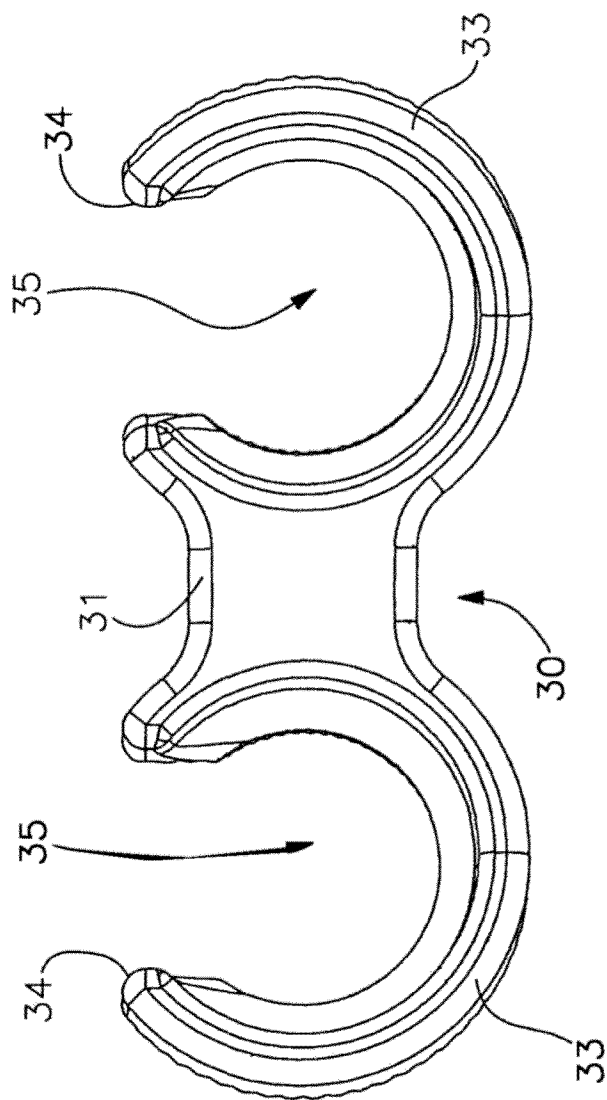

I claim:

1. A multi-link spinal treatment system comprising:
    bone fasteners having a bone screw portion, a shoulder and a locknut receiving portion, the locknut receiving portion having a diameter and a bone fastener axis;
    longitudinal linking members, each of the longitudinal linking members comprising a main body having a longitudinal axis and two apertured ends having apertures sized to receive the locknut receiving portion therethrough, wherein the two apertured ends include a slotted apertured end comprising a slot having a width greater than the diameter of the locknut receiving portion and a non-slotted apertured end, wherein each longitudinal linking member main body is stepped defining an upper stepped portion comprising the non-slotted apertured end and a lower stepped portion comprising the slotted apertured end, wherein the upper stepped portion is stepped to a height of the slotted apertured end of the lower stepped portion such that a non-slotted apertured end of a first longitudinal linking member is configured for placement atop a slotted apertured end of a second longitudinal linking member;
    end caps, each of the end caps comprising an aperture sized to receive the locknut receiving portion therethrough, at least one of the end caps being a slotted end cap comprising a slot having a width greater than the diameter of the locknut receiving portion; and
    locknuts mounted onto the locknut receiving portions of the bone fasteners, the lock nuts securing the longitudinal linking members and the end caps against the shoulders of the bone fasteners, wherein a locknut presses the non-slotted apertured end of the first longitudinal linking member against the slotted apertured end of the second longitudinal linking member;
    whereby after loosening but not removing one of the lock nuts from the bone fasteners, one of the slotted end caps is removable from the locknut receiving portion by movement in the direction perpendicular to the bone fastener axis, and further whereby the slotted apertured end of one of the longitudinal linking members is mountable onto the locknut receiving portion in place of the removed slotted end cap by movement in the direction perpendicular to the bone fastener axis.

2. The multi-link spinal treatment system of claim 1, further comprising one or more transverse linking members comprising a main body having a longitudinal axis and two apertured ends having apertures sized to receive the locknut receiving portion therethrough, at least one or more of the transverse linking members being a slotted transverse linking member wherein each of the apertured ends comprises a slot having a width greater than the diameter of the locknut receiving portion;
    wherein some of the locknuts mounted onto the locknut receiving portions of the bone fasteners secure the longitudinal linking members and the one or more transverse linking members against the shoulders of the bone fasteners;
    whereby after loosening but not removing two of the lock nuts from the bone fasteners, one of the slotted transverse linking members is removable from the locknut receiving portions by movement in the direction perpendicular to the bone fastener axis, and further whereby the slotted apertured end of one of the longitudinal linking members is mountable onto the locknut receiving portion in place of the removed transverse linking member by movement in the direction perpendicular to the bone fastener axis.

3. The multi-link spinal treatment system of claim 2, wherein the slot of the apertured slotted end of the longitudinal linking member is oriented in the direction of the main body longitudinal axis of the longitudinal linking member.

4. The multi-link spinal treatment system of claim 3, wherein each of the slots of the apertured ends of the slotted transverse linking member is oriented in the direction perpendicular to the main body longitudinal axis of the transverse linking member.

5. The multi-link spinal treatment system of claim 2, wherein each of the slots of the apertured ends of the slotted transverse linking member is oriented in the direction perpendicular to the main body longitudinal axis of the transverse linking member.

6. The multi-link spinal treatment system of claim 2, wherein the apertured ends of the longitudinal linking members and the apertured ends of the transverse linking members comprise mating surfaces, the mating surfaces comprising anti-rotation structures.

7. The multi-link spinal treatment system of claim 1, wherein the slot of the apertured slotted end of the longitudinal linking member is oriented in the direction of the main body longitudinal axis of the longitudinal linking member.

8. The multi-link spinal treatment system of claim 1, wherein the apertured ends of the longitudinal linking members and the apertured ends of the end caps comprise mating surfaces, the mating surfaces comprising anti-rotation structures.

9. A method of treating spinal conditions comprising the steps of:
  providing a multi-link spinal system, the multi-link spinal system comprising:
    bone fasteners having a bone screw portion, a shoulder and a locknut receiving portion, the locknut receiving portion having a diameter and a bone fastener axis;
    longitudinal linking members, each of the longitudinal linking members comprising a main body having a longitudinal axis and two apertured ends having apertures sized to receive the locknut receiving portion therethrough, at least one of the apertured ends being a slotted apertured end comprising a slot having a width greater than the diameter of the locknut receiving portion;
    end caps, each of the end caps comprising an aperture sized to receive the locknut receiving portion therethrough, at least one of the end caps being a slotted end cap comprising a slot having a width greater than the diameter of the locknut receiving portion; and
    locknuts mounted onto the locknut receiving portions of the bone fasteners, the lock nuts securing the longitudinal linking members and the end caps against the shoulders of the bone fasteners;
    whereby after loosening but not removing one of the lock nuts from the bone fasteners, one of the slotted end caps is removable from the locknut receiving portion by movement in the direction perpendicular to the bone fastener axis, and further whereby the slotted apertured end of one of the longitudinal linking members is mountable onto the locknut receiving portion in place of the removed slotted end cap by movement in the direction perpendicular to the bone fastener axis;
  implanting the bone screw portions of the bone fasteners into vertebrae;
  forming a chain of longitudinal linking members by mounting longitudinal linking members in overlapping manner onto adjacent bone fasteners such that the locknut receiving portions of the bone fasteners extend through the apertured ends of the longitudinal linking members;
  installing locknuts onto the locknut receiving portions of the bone fasteners having overlapping longitudinal members;
  installing end caps either above or below the longitudinal linking members onto the locknut receiving portions of the bone fasteners not having overlapping longitudinal members, wherein at least one of the end caps is a slotted end cap;
  installing locknuts onto the locknut receiving portions of the bone fasteners having end caps;
  implanting the bone screw portions of one or more additional bone fasteners into vertebrae;
  loosening but not removing one or more of the locknuts installed on the locknut receiving portions of the bone fasteners retaining slotted end caps;
  removing one or more of the slotted end caps from the locknut receiving portions of the bone fasteners by movement in the direction perpendicular to the bone fastener axis;
  inserting the slotted apertured ends of one or more of the longitudinal linking members onto the locknut receiving portions of the bone fasteners in place of the removed slotted end caps by movement in the direction perpendicular to the bone fastener axis, and mounting the one or more longitudinal linking members on the one or more additional bone fasteners; and
  tightening the loosened one or more locknuts.

10. A method of treating spinal conditions comprising the steps of:
  providing a multi-link spinal system, the multi-link spinal system comprising:
    bone fasteners having a bone screw portion, a shoulder and a locknut receiving portion, the locknut receiving portion having a diameter and a bone fastener axis;
    longitudinal linking members, each of the longitudinal linking members comprising a main body having a longitudinal axis and two apertured ends having apertures sized to receive the locknut receiving portion therethrough, at least one of the apertured ends being a slotted apertured end comprising a slot having a width greater than the diameter of the locknut receiving portion;
    end caps, each of the end caps comprising an aperture sized to receive the locknut receiving portion therethrough, at least one of the end caps being a slotted end cap comprising a slot having a width greater than the diameter of the locknut receiving portion;
    locknuts mounted onto the locknut receiving portions of the bone fasteners, the lock nuts securing the longitudinal linking members and the end caps against the shoulders of the bone fasteners; and
    one or more transverse linking members comprising a main body having a longitudinal axis and two apertured ends having apertures sized to receive the locknut receiving portion therethrough, at least one or more of the transverse linking members being a slotted transverse linking member wherein each of the apertured ends comprises a slot having a width greater than the diameter of the locknut receiving portion;
    whereby after loosening but not removing one of the lock nuts from the bone fasteners, one of the slotted end caps is removable from the locknut receiving portion by movement in the direction perpendicular to the bone fastener axis, and further whereby the slotted apertured end of one of the longitudinal linking members is mountable onto the locknut receiving portion in place of the removed slotted end cap by movement in the direction perpendicular to the bone fastener axis;
  wherein some of the locknuts mounted onto the locknut receiving portions of the bone fasteners secure the longitudinal linking members and the one or more transverse linking members against the shoulders of the bone fasteners;

whereby after loosening but not removing two of the lock nuts from the bone fasteners, one of the slotted transverse linking members is removable from the locknut receiving portions by movement in the direction perpendicular to the bone fastener axis, and further whereby the slotted apertured end of one of the longitudinal linking members is mountable onto the locknut receiving portion in place of the removed transverse linking member by movement in the direction perpendicular to the bone fastener axis;

implanting the bone screw portions of the bone fasteners into vertebrae;

forming a chain of longitudinal linking members by mounting longitudinal linking members in overlapping manner onto adjacent bone fasteners such that the locknut receiving portions of the bone fasteners extend through the apertured ends of the longitudinal linking members;

installing locknuts onto the locknut receiving portions of the bone fasteners having overlapping longitudinal members;

installing transverse linking members either above or below the longitudinal linking members onto the locknut receiving portions of the bone fasteners not having overlapping longitudinal members, wherein at least one of the transverse linking members is a slotted transverse linking member;

installing locknuts onto the locknut receiving portions of the bone fasteners having transverse linking members;

implanting the bone screw portions of one or more additional bone fasteners into vertebrae;

loosening but not removing the locknuts installed on the locknut receiving portions of the bone fasteners retaining one of the slotted transverse linking members;

removing the slotted transverse linking member from the locknut receiving portions of the bone fasteners by movement in the direction perpendicular to the bone fastener axis;

inserting the slotted apertured ends of one or more of the longitudinal linking members onto the locknut receiving portions of the bone fasteners in place of the removed slotted transverse linking members by movement in the direction perpendicular to the bone fastener axis, and mounting the one or more longitudinal linking members on the one or more additional bone fasteners; and tightening the loosened one or more locknuts.

11. A method of treating spinal conditions comprising the steps of:

providing a multi-link spinal system, the multi-link spinal system comprising:

bone fasteners having a bone screw portion, a shoulder and a locknut receiving portion, the locknut receiving portion having a diameter and a bone fastener axis;

longitudinal linking members, each of the longitudinal linking members comprising a main body having a longitudinal axis and two apertured ends having apertures sized to receive the locknut receiving portion therethrough, at least one of the apertured ends being a slotted apertured end comprising a slot having a width greater than the diameter of the locknut receiving portion;

end caps, each of the end caps comprising an aperture sized to receive the locknut receiving portion therethrough, at least one of the end caps being a slotted end cap comprising a slot having a width greater than the diameter of the locknut receiving portion;

locknuts mounted onto the locknut receiving portions of the bone fasteners, the lock nuts securing the longitudinal linking members and the end caps against the shoulders of the bone fasteners; and one or more transverse linking members comprising a main body having a longitudinal axis and two apertured ends having apertures sized to receive the locknut receiving portion therethrough, at least one or more of the transverse linking members being a slotted transverse linking member wherein each of the apertured ends comprises a slot having a width greater than the diameter of the locknut receiving portion;

whereby after loosening but not removing one of the lock nuts from the bone fasteners, one of the slotted end caps is removable from the locknut receiving portion by movement in the direction perpendicular to the bone fastener axis, and further whereby the slotted apertured end of one of the longitudinal linking members is mountable onto the locknut receiving portion in place of the removed slotted end cap by movement in the direction perpendicular to the bone fastener axis;

wherein some of the locknuts mounted onto the locknut receiving portions of the bone fasteners secure the longitudinal linking members and the one or more transverse linking members against the shoulders of the bone fasteners;

whereby after loosening but not removing two of the lock nuts from the bone fasteners, one of the slotted transverse linking members is removable from the locknut receiving portions by movement in the direction perpendicular to the bone fastener axis, and further whereby the slotted apertured end of one of the longitudinal linking members is mountable onto the locknut receiving portion in place of the removed transverse linking member by movement in the direction perpendicular to the bone fastener axis;

implanting the bone screw portions of the bone fasteners into vertebrae;

forming a chain of longitudinal linking members by mounting longitudinal linking members in overlapping manner onto adjacent bone fasteners such that the locknut receiving portions of the bone fasteners extend through the apertured ends of the longitudinal linking members;

installing locknuts onto the locknut receiving portions of the bone fasteners having overlapping longitudinal members;

installing either end caps or transverse linking members either above or below the longitudinal linking members onto the locknut receiving portions of the bone fasteners not having overlapping longitudinal members, wherein at least one of the end caps is a slotted end cap or at least one of the transverse linking members is a slotted transverse linking member;

installing locknuts onto the locknut receiving portions of the bone fasteners having end caps or transverse linking members;

implanting the bone screw portions of one or more additional bone fasteners into vertebrae;

loosening but not removing the locknuts installed on the locknut receiving portions of the bone fasteners retaining the at least one slotted end cap or the at least one slotted transverse linking members;

removing the at least one slotted end cap or the at least one slotted transverse linking member from the locknut receiving portions of the bone fasteners by movement in the direction perpendicular to the bone fastener axis;

inserting the slotted apertured ends of one or more of the longitudinal linking members onto the locknut receiving portions of the bone fasteners in place of the removed at least one slotted end cap or the at least one slotted transverse linking member by movement in the direction perpendicular to the bone fastener axis, and mounting the one or more longitudinal linking members on the one or more additional bone fasteners; and tightening the loosened one or more locknuts.

\* \* \* \* \*

UNITED STATES PATENT AND TRADEMARK OFFICE
CERTIFICATE OF CORRECTION

PATENT NO. : 11,849,980 B2
APPLICATION NO. : 16/909275
DATED : December 26, 2023
INVENTOR(S) : Chaim Rogozinski It is certified that error appears in the above-identified patent and that said Letters Patent is hereby corrected as shown below:

On the Title Page

Figure 2:
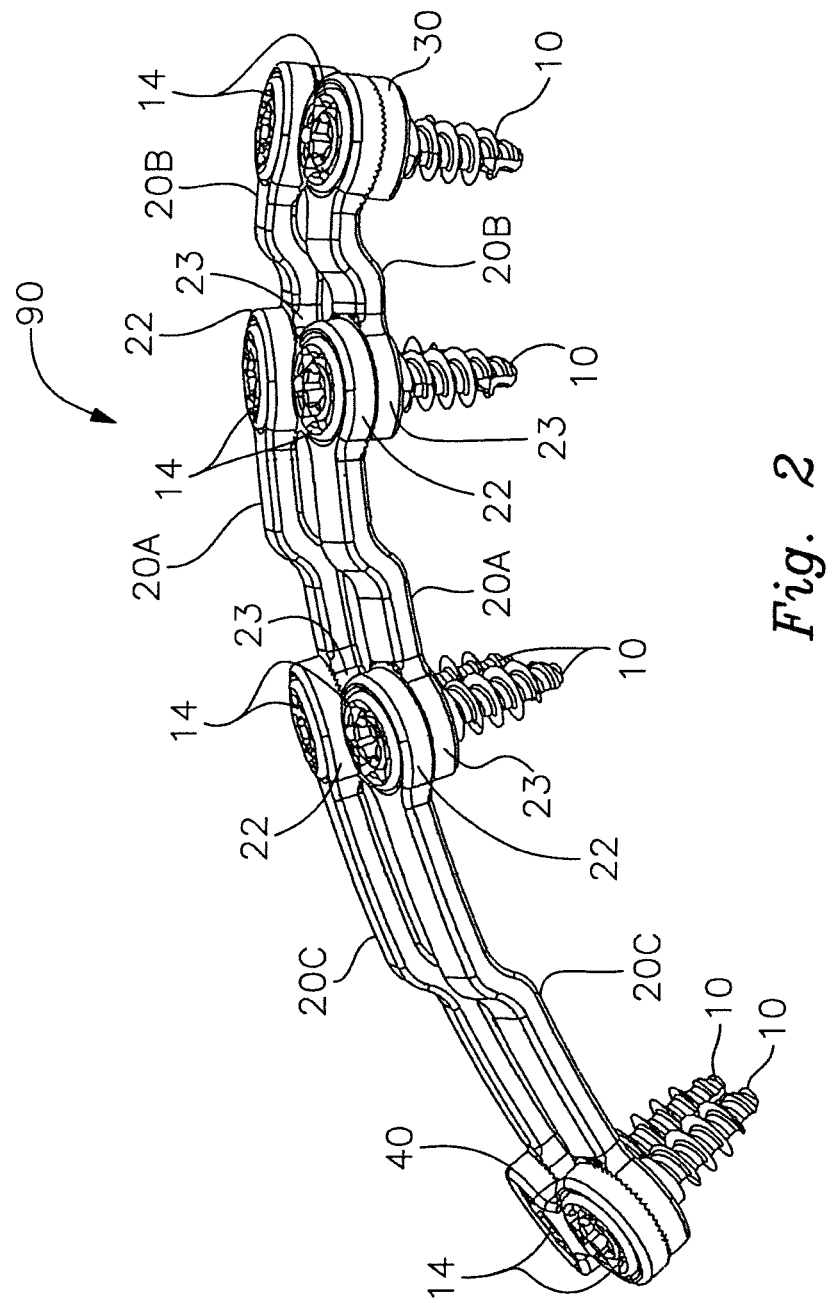
Figure 3:
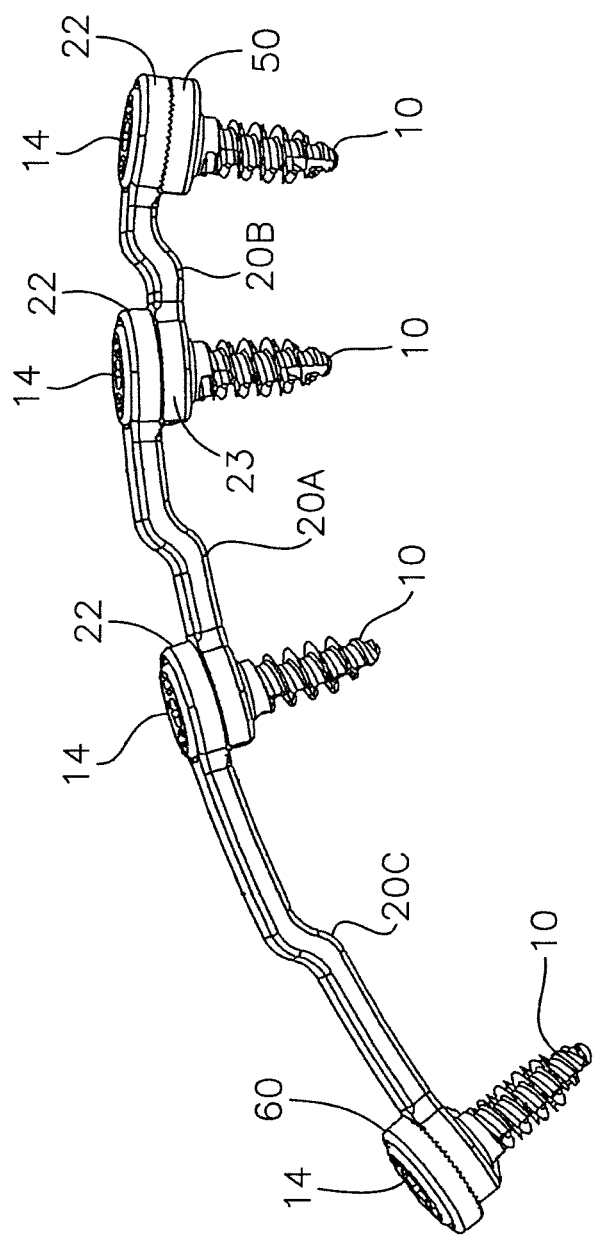
Figure 4:
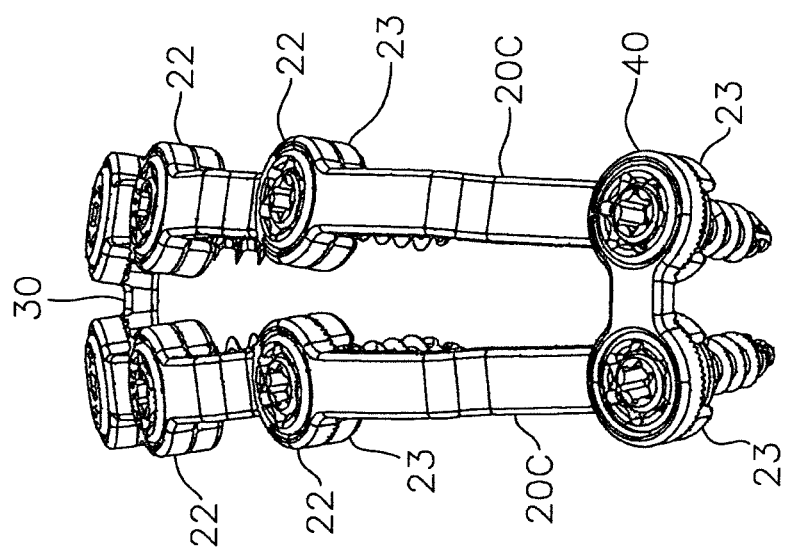
Figure 5:
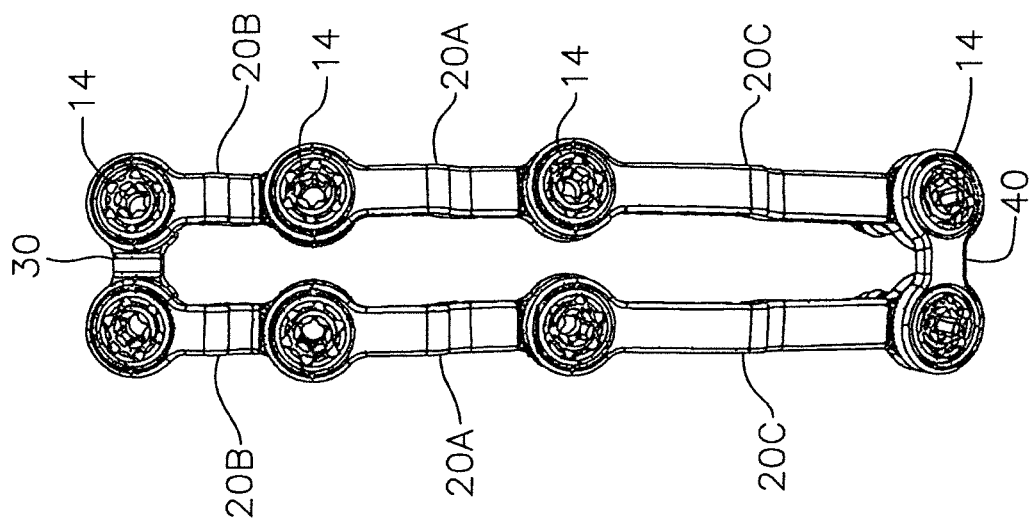
Figure 6:
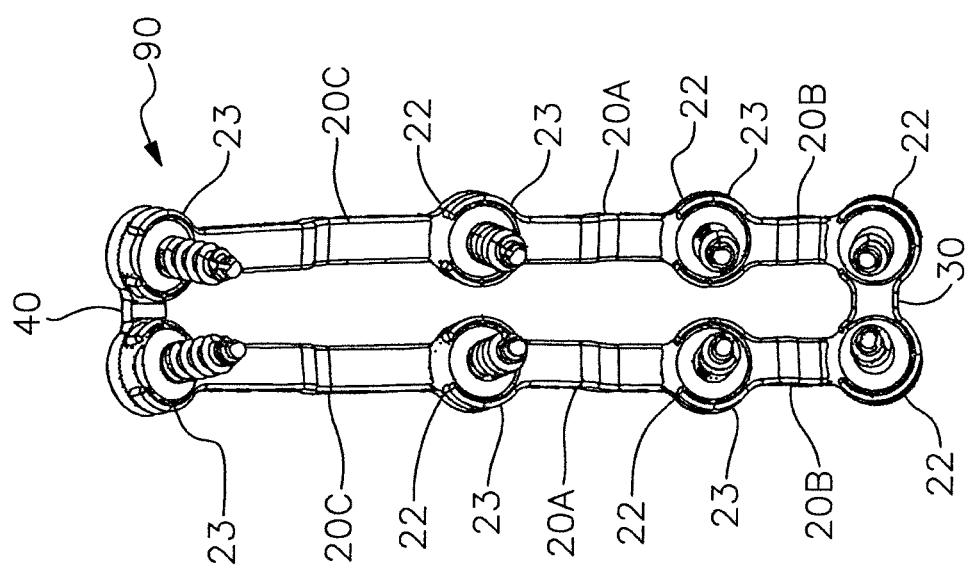
Figure 7:
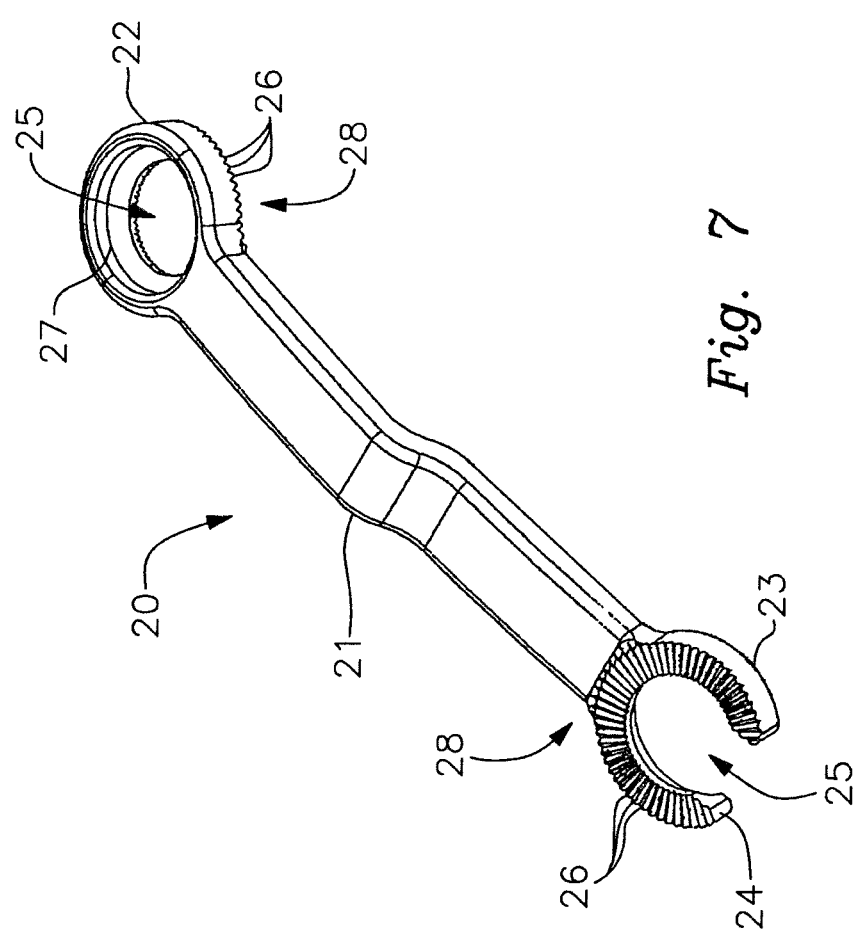
FIGS. 7-10 illustrate a representative longitudinal linking member.
Figure 8:
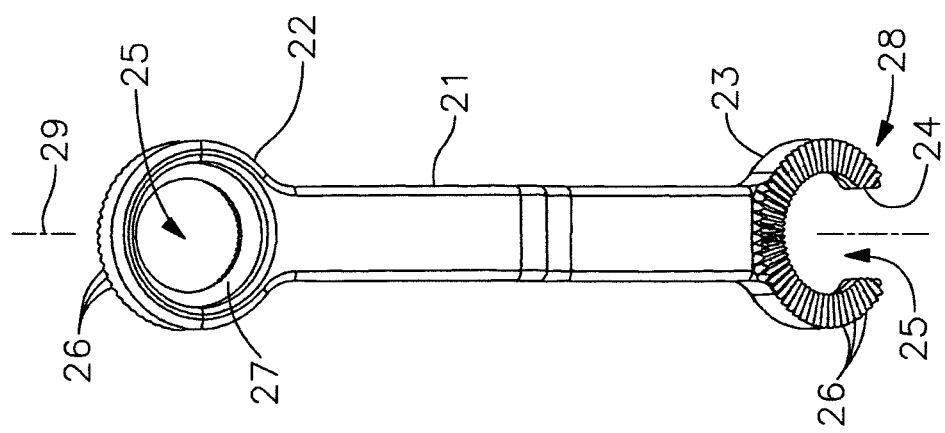
Figure 9:
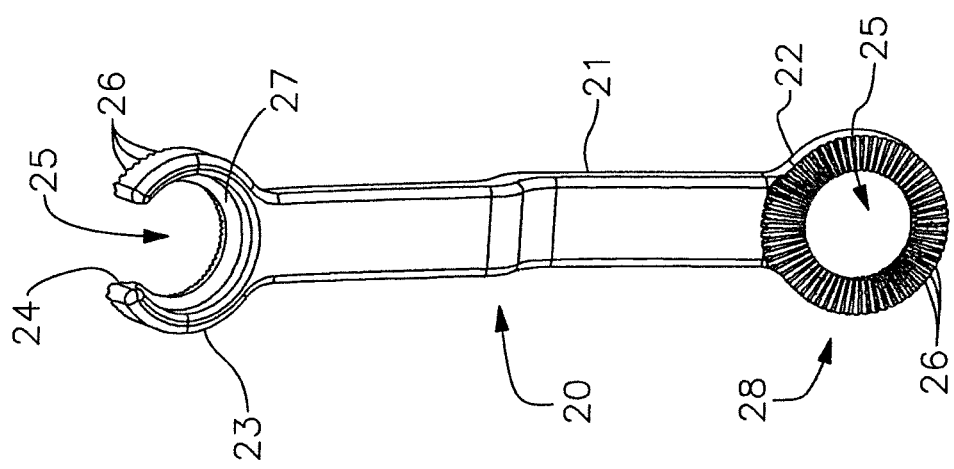
Figure 10:
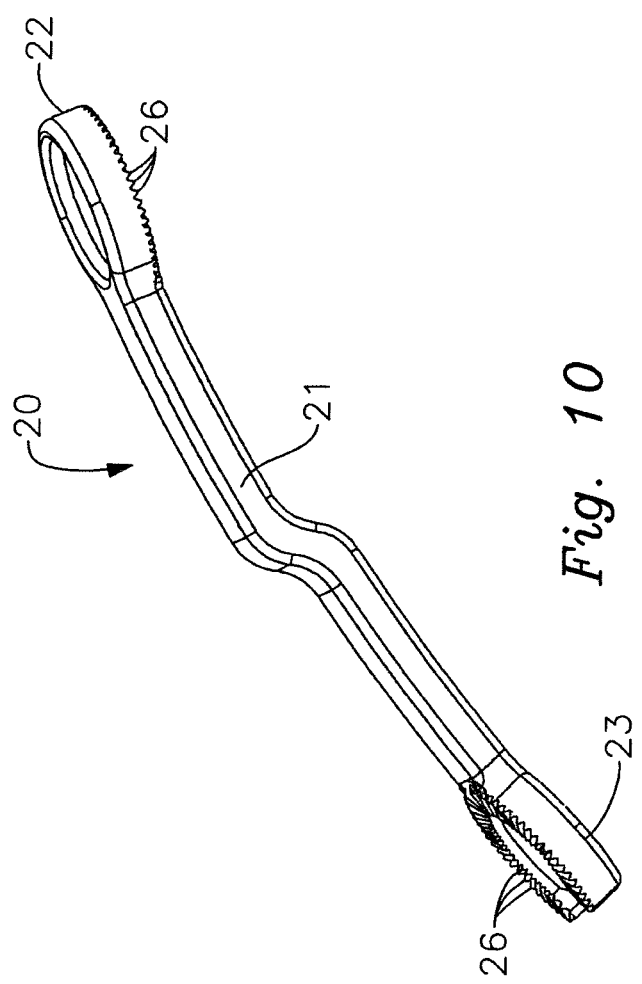
Figure 11:
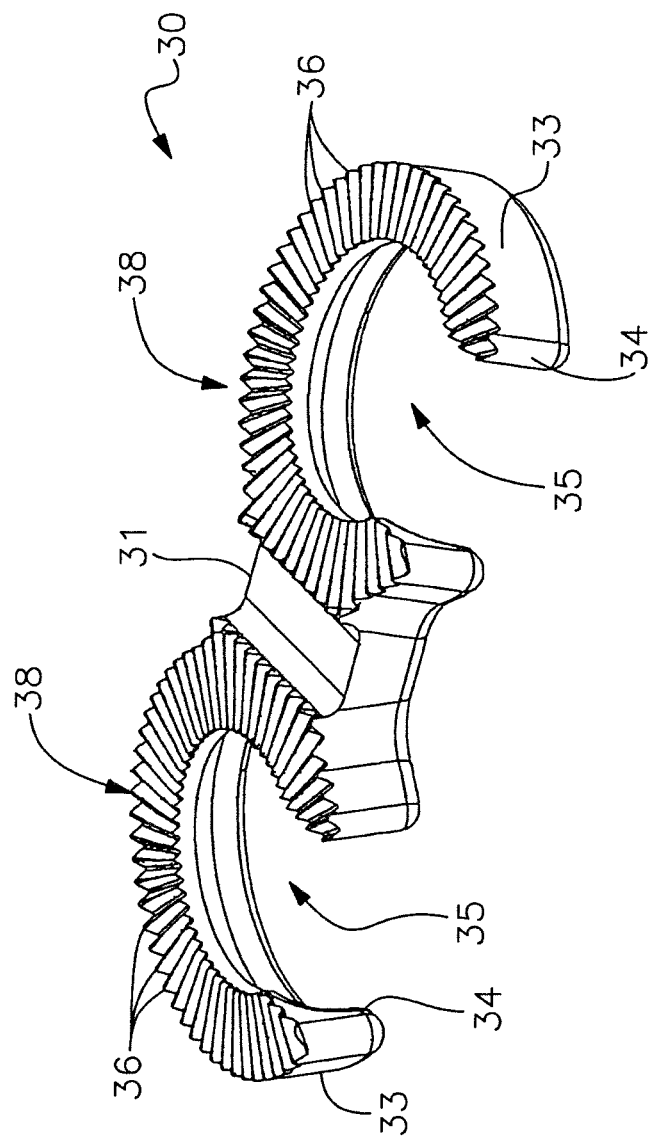
FIGS. 11-14 illustrate a representative transverse linking member having slotted apertured ends.
Figure 12:
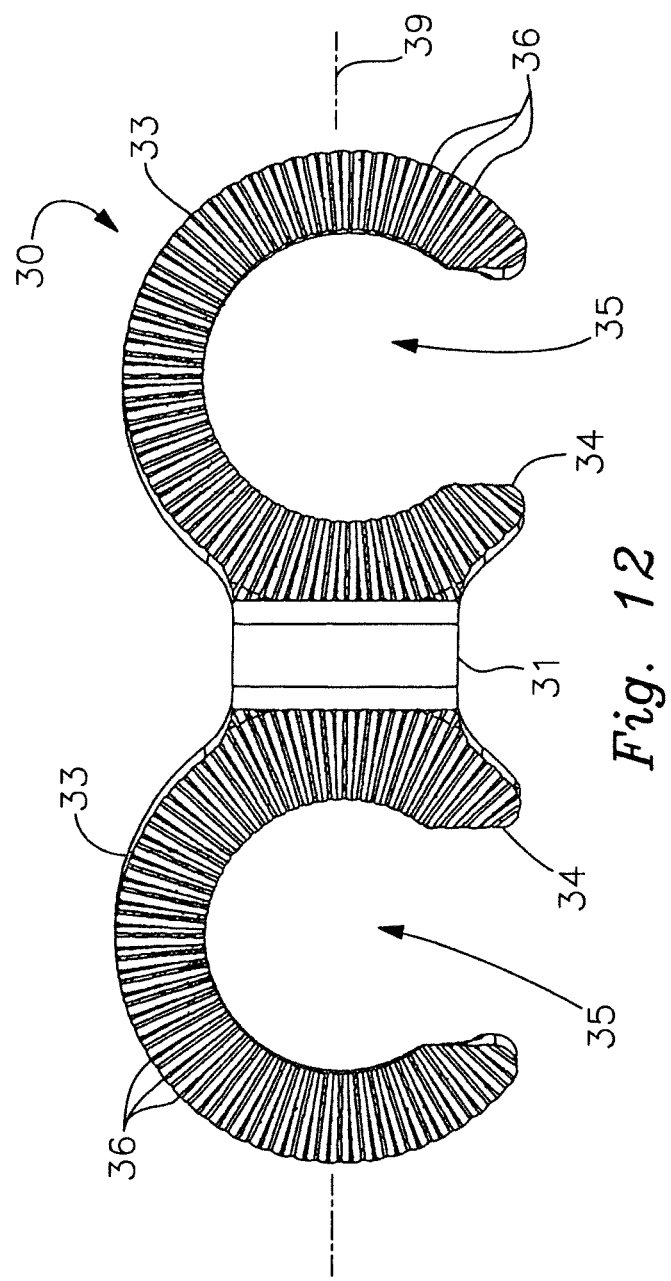
Figure 13:
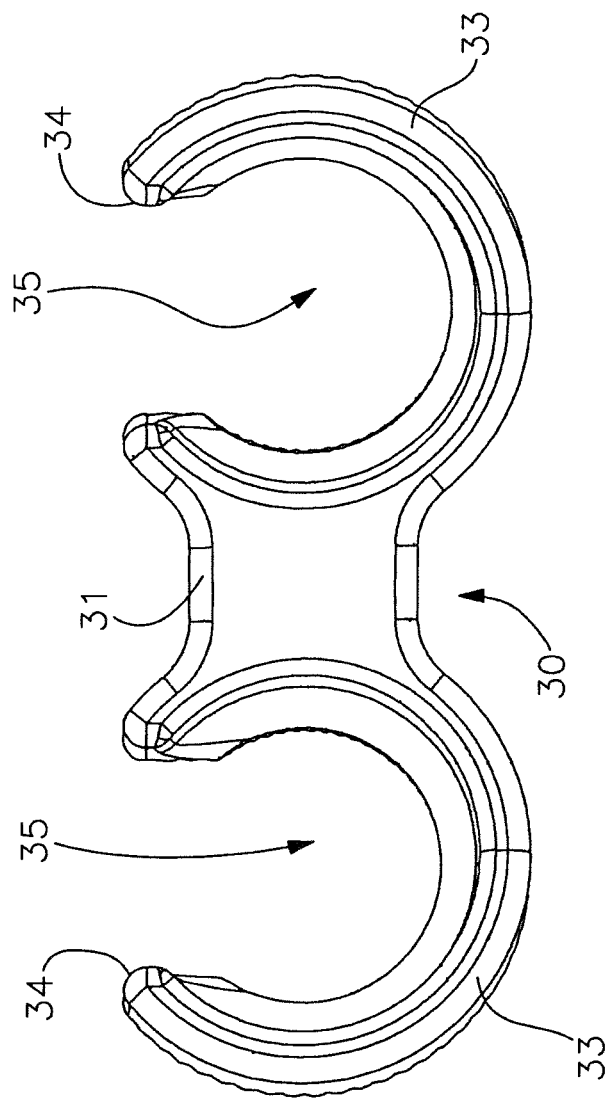
Figure 14:
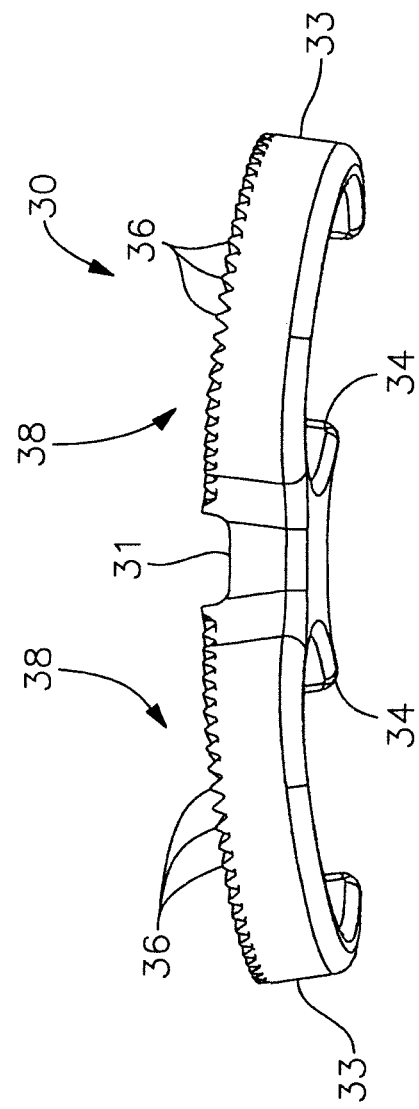
Figure 15:
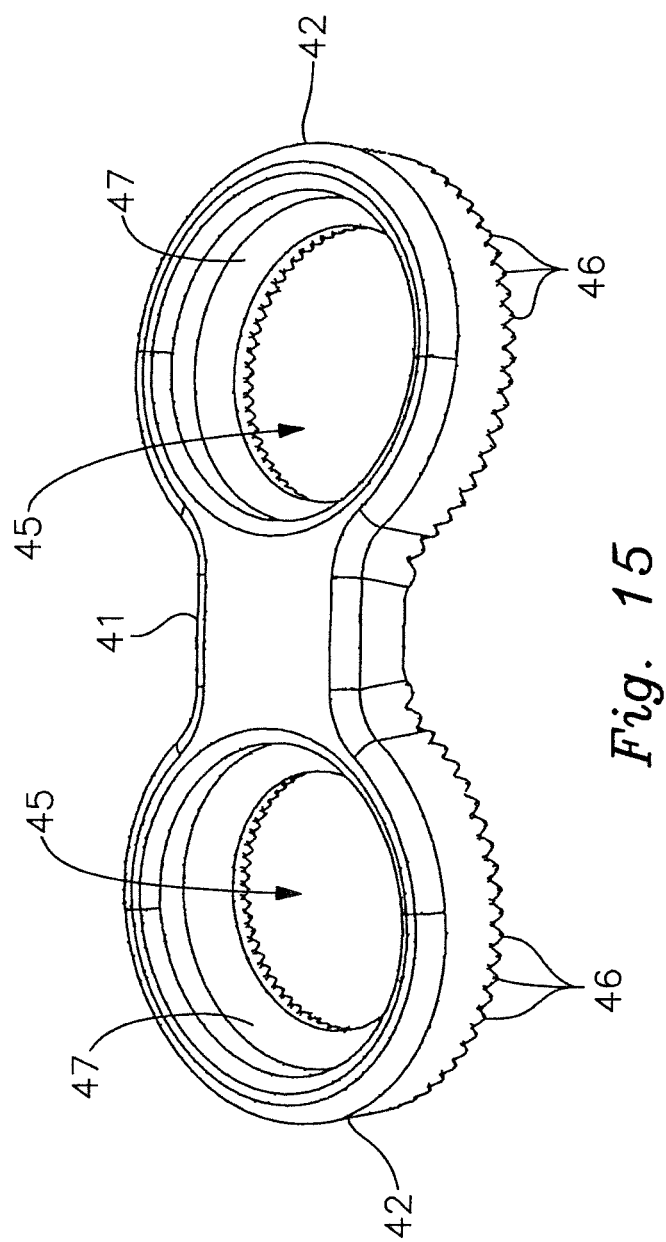
FIGS. 15-18 illustrate a representative transverse linking member having closed apertured ends.
Figure 16:
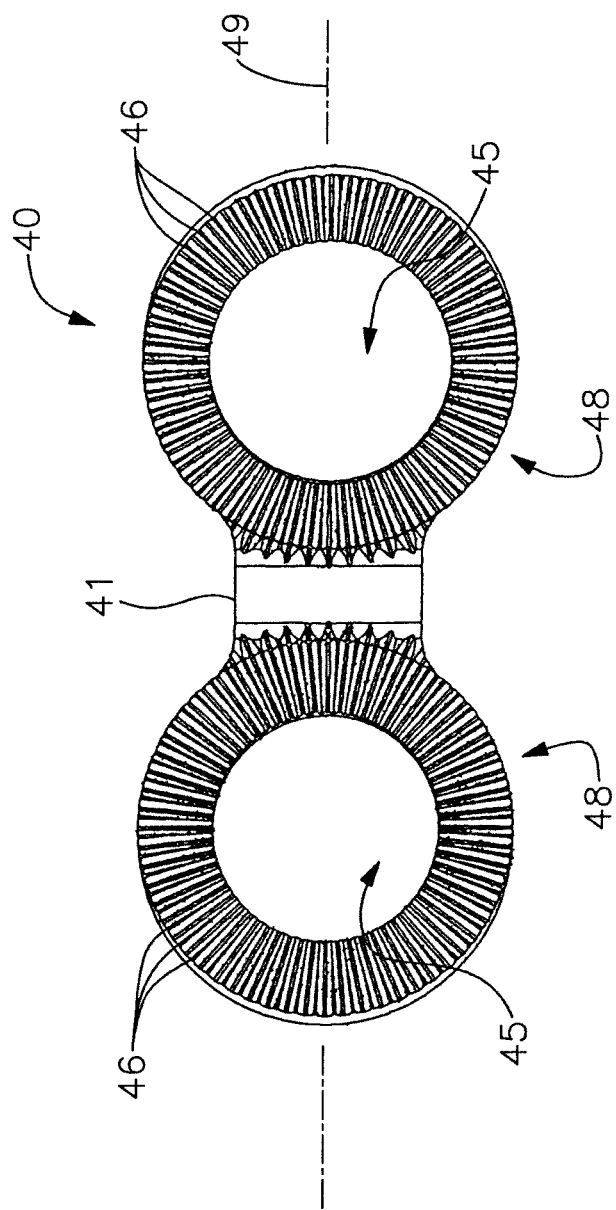
Figure 17:
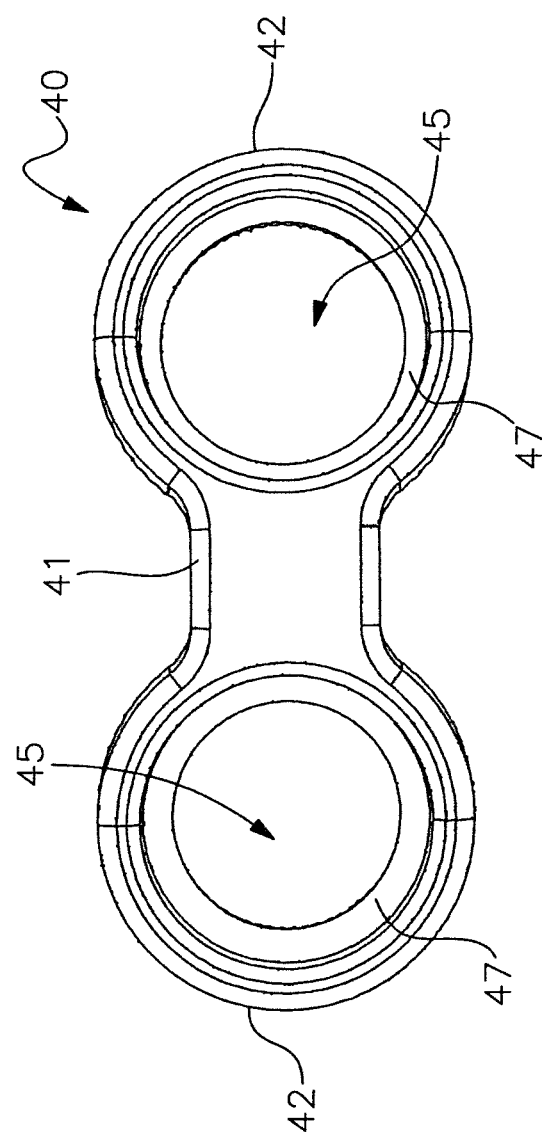
Figure 20:
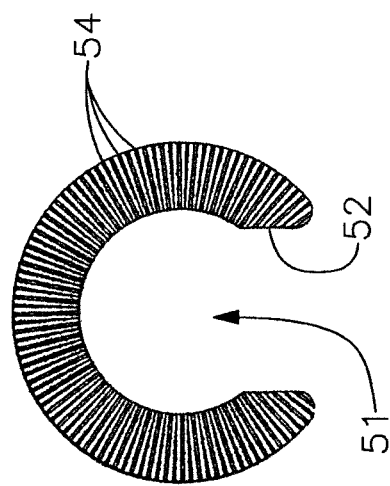
FIGS. 19-21 illustrate a representative slotted end cap member.
Figure 19:
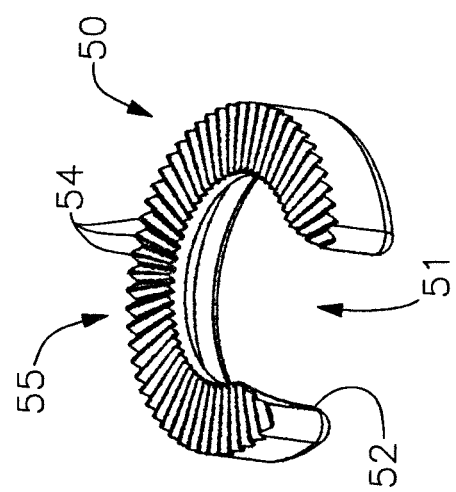

Replace the illustrative print figure, FIG 2, with the FIG 2 shown on the attached drawing sheets In the Drawings Twenty Three Replacement Drawing Sheets are attached to correct FIGS 1 - 27

Signed and Sealed this
Ninth Day of April, 2024

Katherine Kelly Vidal
*Director of the United States Patent and Trademark Office*